United States Patent
Otokuni et al.

(10) Patent No.: US 9,036,774 B2
(45) Date of Patent: May 19, 2015

(54) PRESS PLATE AND RADIOGRAPHIC IMAGING APPARATUS

(71) Applicant: FUJIFILM CORPORATION, Minato-ku, Tokyo (JP)

(72) Inventors: Shinji Otokuni, Kanagawa (JP); Kenji Takata, Kanagawa (JP); Tomoki Inoue, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/139,878

(22) Filed: Dec. 24, 2013

(65) Prior Publication Data

US 2014/0177791 A1    Jun. 26, 2014

(30) Foreign Application Priority Data

Dec. 26, 2012    (JP) .................................. 2012-283698

(51) Int. Cl.
*A61B 6/04*    (2006.01)
*A61B 6/00*    (2006.01)

(52) U.S. Cl.
CPC . *A61B 6/04* (2013.01); *A61B 6/502* (2013.01); *A61B 6/0414* (2013.01)

(58) Field of Classification Search
CPC .............................. A61B 6/0414; A61B 6/502
USPC .............................. 378/37, 208; 600/427, 445
See application file for complete search history.

(56) References Cited

U.S. PATENT DOCUMENTS

| 4,943,986 A | 7/1990 | Barbarisi |
| 5,664,573 A | 9/1997 | Shmulewitz |
| 2005/0008117 A1 * | 1/2005 | Livingston ...................... 378/37 |
| 2008/0080668 A1 | 4/2008 | Kashiwagi |
| 2012/0130173 A1 | 5/2012 | Lutze et al. |

FOREIGN PATENT DOCUMENTS

| CN | 102448359 | 5/2012 |
| JP | 2011-206438 A | 10/2011 |

OTHER PUBLICATIONS

Extended European Search Report dated Apr. 10, 2014 from the EPO in an European patent application corresponding to the instant patent application.

Office action dated Jan. 13, 2015 from SIPO in the corresponding Chinese patent application, with English translation. This office action translation is submitted now in order to supplement the understanding of the cited references which are being disclosed in the instant Disclosure Statement.

* cited by examiner

*Primary Examiner* — David J Makiya
*Assistant Examiner* — Dani Fox
(74) *Attorney, Agent, or Firm* — Solaris Intellectual Property Group, PLLC

(57) ABSTRACT

A press plate that includes: a plate shaped press portion that is capable of resilient deformation; a first slit that is provided to a first wall portion of a support body with length direction along a first edge portion of the press portion, and that penetrates the first wall portion; second slits that are provided to a second wall portions of the support body with length direction along second edge portions of the press portion, and that penetrate the second wall portions; and a first corner portion slit that is provided straddling a corner portion between the first wall portion and the second wall portion and penetrating the corner portion, that is connected to the first slit, and that is disposed at a separation to the second slit.

13 Claims, 34 Drawing Sheets

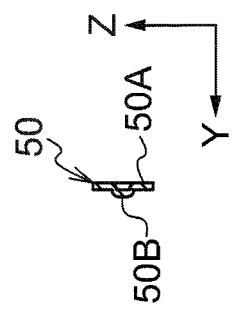
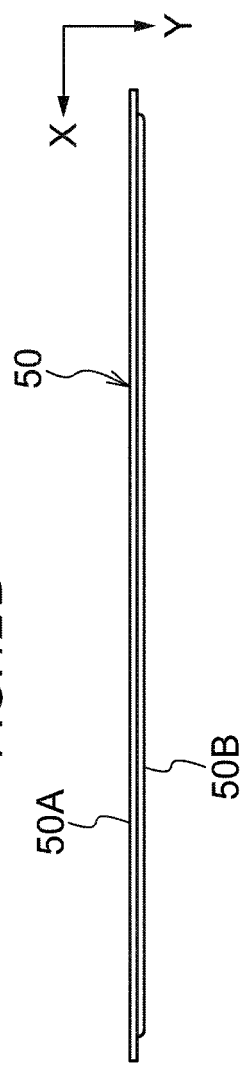
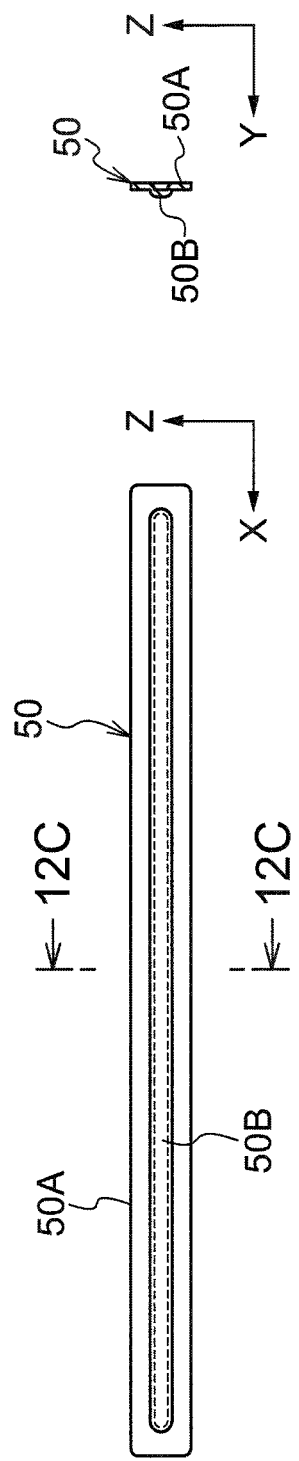

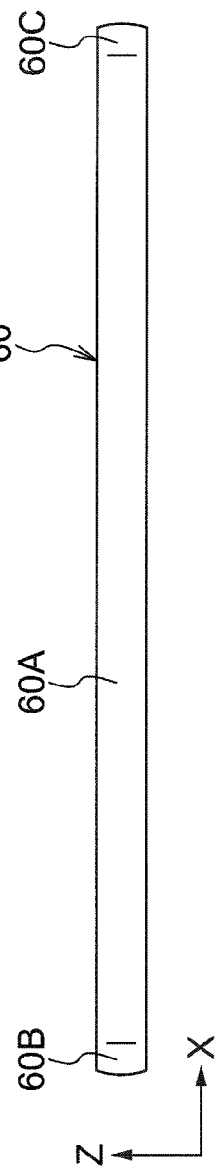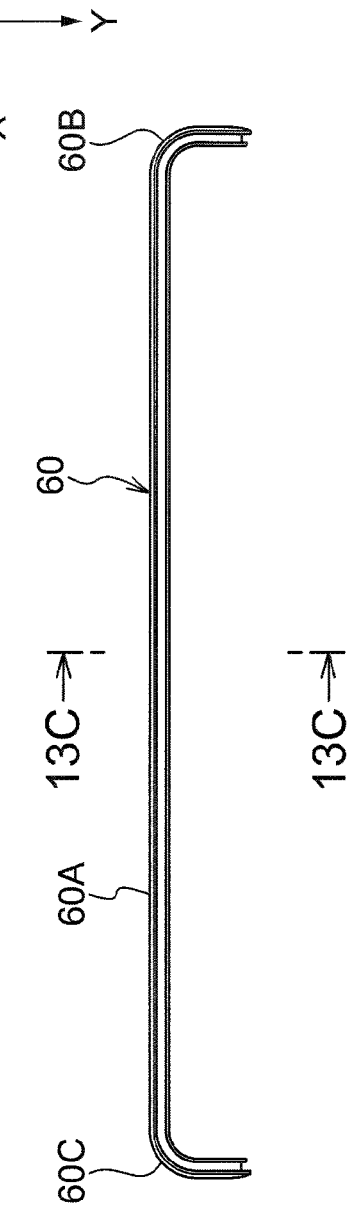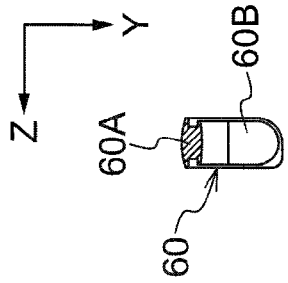

PRESS PLATE AND RADIOGRAPHIC IMAGING APPARATUS

CROSS-REFERENCE TO RELATED APPLICATION

This application claims priority under 35 USC 119 from Japanese Patent Application No. 2012-283698 filed on Dec. 26, 2012, the disclosure of which is incorporated by reference herein.

BACKGROUND OF THE INVENTION

1. Technical Field

The present invention relates to a press plate and a radiographic imaging apparatus, and in particular relates to a press plate for performing image capture with an image capture body in a compressed state, and to a radiographic imaging apparatus provided with such a press plate.

2. Related Art

Mammography apparatuses for early detection of breast cancer and the like are known as medical radiographic imaging apparatuses. In mammography apparatuses, the breast of an examinee is interposed as an image capture body between an imaging face of an imaging table and a press plate, and then a radiographic image is captured with the breast in a state compressed by the press plate. Adopting such an imaging method makes the thickness of the breast thinner, and so enables a clear radiographic image to be obtained and enables the radiation amount to be reduced.

In Japanese Patent Application Laid-Open (JP-A) No. 2011-206438, a radiographic imaging apparatus and a press plate for a radiographic imaging apparatus are described that enable the burden on an examinee during breast pressing, and in particular the pain felt by the examinee, to be reduced. The press plate is equipped with a flexible press plate section that presses the breast against the imaging face of an imaging table, a reinforcement plate section that is integrally formed at both ends of the press plate section, and a support plate section that spans across the reinforcement plate section and maintains a gap to the press plate section.

In the press plate described in JP-A No. 2011-206438, a location at which flexibility can be obtained is limited to a portion of the press plate section where the gap to the support plate section is maintained. Since no gap is provided at the reinforcement plate section, rigidity is increased at locations of the press plate section that are integrally formed with the reinforcement plate section, such that flexibility is not readily obtained and compression force becomes stronger. Moreover, since the rigidity of a corner portion between the support plate section and the reinforcement plate section is higher than the rigidity of the support plate section and the reinforcement plate section due to the shape of the corner portion, flexibility is even less readily obtained and compression force readily concentrates at the corner portion. There is consequently room for improvement in the press plate when it comes to obtaining appropriate deflection in the press plate section. Providing a gap between the support plate section and the press plate section along the reinforcement plate section may be considered when attempting simply to obtain flexibility. However, distortion (or twisting) between the support plate section and reinforcement plate section and the press plate section occurs when compression force is applied to the support plate section and the reinforcement plate section.

SUMMARY

An aspect of the present invention is a press plate that includes: a plate shaped press portion that is capable of resilient deformation; a support body including a first wall portion standing from one edge portion of the press portion further upwards than a press portion plate face, and second wall portions extending from both ends of the first wall portion to face each other along other edge portions of the press portion so as to stand up from the other edge portions, and the support body supporting the press portion; a first slit that is provided to the first wall portion with length direction along the one edge portion, and that penetrates the first wall portion; second slits that are provided to the second wall portions with length direction along the other edge portions, and that penetrate the second wall portions; and a first corner portion slit that is provided straddling a corner portion between the first wall portion and the second wall portion and penetrating the corner portion, that is connected to the first slit, and that is disposed at a separation to the second slit.

BRIEF DESCRIPTION OF THE DRAWINGS

FIG. 12A is a front face view of a reinforcement member provided to a press plate of the first exemplary embodiment, FIG. 12B is a plan view of the reinforcement member illustrated in FIG. 12A, and FIG. 12C is a cross-section illustrating the reinforcement member illustrated in FIG. 12A taken along line 12C-12C and viewed along the direction indicated by the arrows;

FIG. 13A is a front face view illustrating a gap member provided to a first slit and a first corner portion slit of the press plate illustrated in FIG. 2, FIG. 13B is a plan view of the gap member illustrated in FIG. 13A, and FIG. 13C is a cross-section illustrating the gap member illustrated in FIG. 13B, taken along line 13C-13C and viewed from the direction indicated by the arrows;

DETAILED DESCRIPTION OF THE INVENTION

Figure 1:
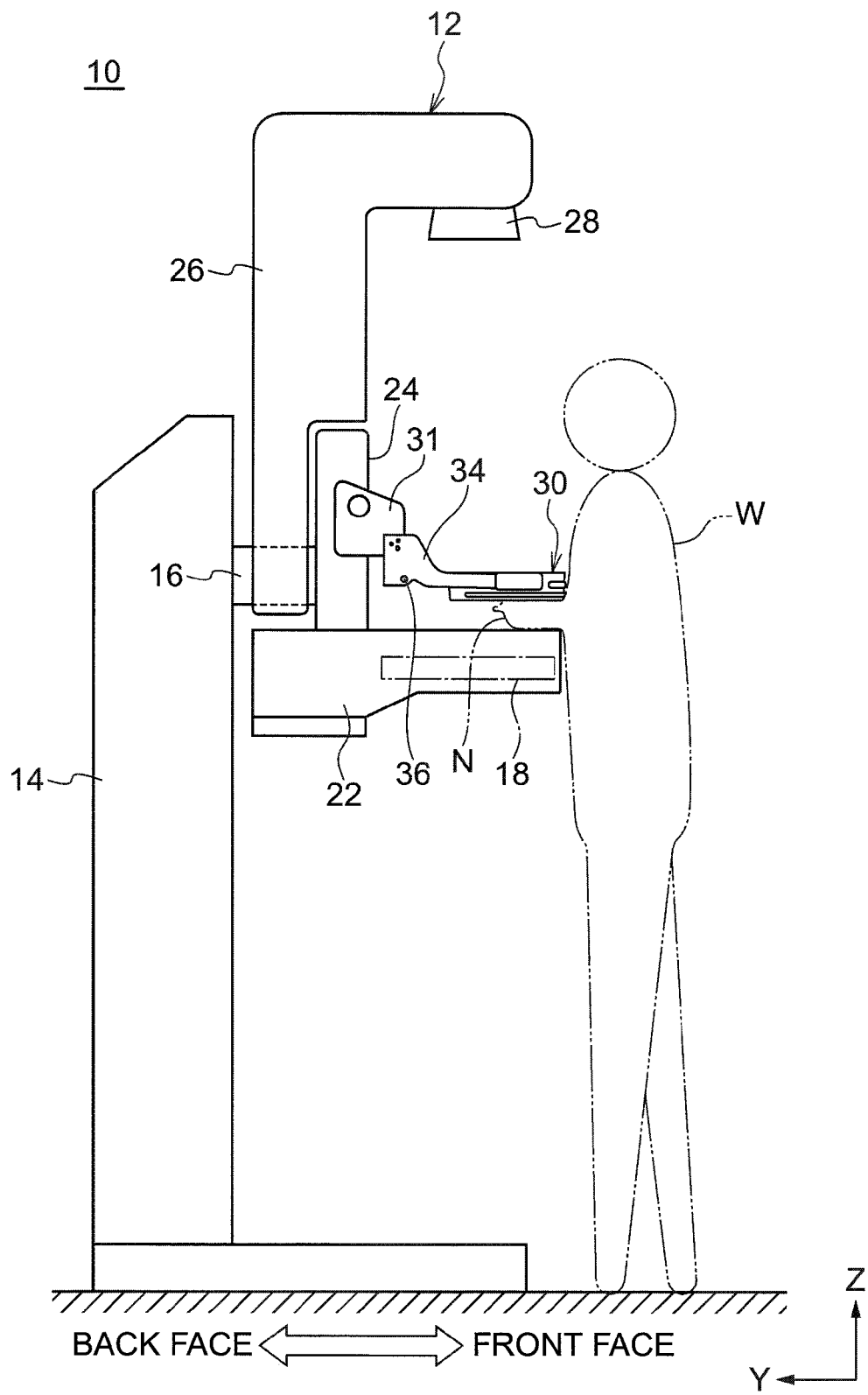
FIG. 1 is a schematic side view illustrating an overall configuration of a radiographic imaging apparatus according to a first exemplary embodiment of the present invention.

Explanation follows regarding exemplary embodiments of the present invention, with reference to the attached drawings. Note that configuration elements with similar functions are allocated the same reference numerals in the drawings, and repeated explanation thereof is omitted as appropriate. The direction denoted by X in the drawings illustrates as appropriate the direction from the left side towards the right side as viewed by an examinee (imaging subject) who is in a state oriented facing towards a radiographic imaging apparatus for radiographic imaging. Similarly, the direction denoted by Y illustrates the direction from the front side (chest wall side) of the examinee towards a back face side of the radiographic imaging apparatus, and the direction denoted by Z in the drawings illustrates the direction from the side below the feet of the examinee towards the upper side of the radiographic imaging apparatus. Namely, the labels X, Y, Z respectively indicate directions corresponding to an X axis, a Y axis and a Z axis in an XYZ coordinate system.

First Exemplary Embodiment

In a first exemplary embodiment of the present invention, an example will be explained in which the present invention is applied to a mammography apparatus serving as a radiographic imaging apparatus, and to a press plate incorporated therein.

Radiographic Imaging Apparatus Overall Configuration

As illustrated in FIG. 1, a radiographic imaging apparatus 10 according to the first exemplary embodiment is a mammography apparatus. The radiographic imaging apparatus 10 is configured to capture an image of a breast (image capture body) N of an examinee W by radiation irradiation while the examinee is in an upright state. Note that the radiographic imaging apparatus 10 is capable of separately imaging the left and right breasts N of the examinee W who is in a seated state on a seat such as a wheelchair, wherein only the upper body of the examinee W is in an upright state.

The radiographic imaging apparatus 10 is equipped with an imaging section 12 that is substantially C-shaped in side view and is provided at a front face (chest wall of the examinee W) side, and a base section 14 that is disposed further towards the Y direction (back face) side than the imaging section 12 and supports the imaging section 12 from the back face side. From the lower side to the upper side along the Z direction, the imaging section 12 is equipped with: an imaging table 22; a holder 24; a press plate 30; and a support section 26. An uppermost portion of the imaging table 22 is equipped with an imaging face 20 that makes contact with a lower portion of the breast N of the examinee W. In this example the shape of the imaging face 20 is rectangular in plan view, however there is no particular limitation to the shape thereof. From the perspectives of radiation permeability and mechanical strength, at least the imaging face 20 is formed from for example a carbon fiber reinforced plastic. The imaging table 22 is supported at a lower side of the holder 24. The press plate 30 is supported interposed between a support base member 31 and a support arm 34 at an upper side of the imaging table 22 of the holder 24.

The press plate 30 is configured so as to interpose the breast N between the press plate 30 and the imaging face 20, and to compress the breast N from a top portion side. Detailed explanation of the structure of the press plate 30 is given later, however the press plate 30 is formed as a hollow, bottomed rectangular column that opens upwards. Although not particularly provided in the first exemplary embodiment, the press plate 30 may be provided with a lid member to close off the open upper portion. The press plate 30 is configured movable in the vertical direction (Z direction) with respect to the imaging face 20. The press plate 30 is also provided with an adjustment component that enables rotation of the press plate 30 about a rotation shaft 36 that is provided between the support base member 31 and the support arm 34. The adjustment component is capable of adjusting the angle between an opposing face of a press portion 32 (see FIG. 2) of the press plate 30 and the imaging face 20, and can set a parallel state or an inclined state of the press portion 32 with respect to the imaging face 20. The adjustment component tilts the press portion 32 so as to hold the breast N widening out a base side (chest wall side) of the breast N, thereby reducing the pain felt by the examinee W when the breast N is compressed. An angle detection sensor is provided to the rotation shaft 36 or in the vicinity thereof, to detect the compression tilt angle.

The support section 26 is provided above the holder 24 as a separate component to the holder 24 and is substantially configured in an inverted L-shape in side view. A radiation irradiation section 28 is provided at the upper side of the support section 26, facing towards the imaging face 20, and is capable of irradiating radiation for imaging or for measurement. A radiation detector 18 is provided facing the radiation irradiation section 28 inside the imaging table 22. The radiation detector 18 receives radiation that has passed from the radiation irradiation section 28 through the press plate 30, the breast N and the imaging face 20 and carries image data of the breast N, and detects the image data. In the radiographic imaging apparatus 10 of the present exemplary embodiment, X-rays are employed as the radiation. Note that in the present invention there is no limitation of the radiation to X-rays. For example, radiation includes at least radiations employed in medical consultation, such as gamma rays, an electron beam, a neutron beam, a proton beam and a heavy particle beam.

A rotation shaft 16 is provided to the upper side of the base section 14 so as to extend towards the front face side along a horizontal direction. The support section 26 and the holder 24 are rotatably supported by the rotation shaft 16. Namely, the imaging section 12 including the support section 26 is capable of rotation about the rotation shaft 16 with respect to the base section 14.

It is also possible to switch between a coupled state of the rotation shaft 16 and the holder 24 together, and an uncoupled state of the rotation shaft 16 and the holder 24. In order to incarnate such switching, for example, a gear wheel is provided to the rotation shaft 16 and the holder 24 that is switchable between a meshed state and an unmeshed state. In the coupled state, the holder 24 rotates accompanying rotation of the rotation shaft 16, and in the uncoupled state, the holder 24 is free to rotate with respect to rotation of the rotation shaft 16. The rotational force of the rotation shaft 16 is transmitted from a drive source, for example an electric motor, provided inside the base section 14.

Press Plate Configuration

As illustrated in detail in FIG. 2 to FIG. 8, the press plate 30 includes the press portion 32, and a support body 33 that is integrally configured to the press portion 32 and provided above the press portion 32 (in the Z direction), and that supports the press portion 32. The support body 33 includes a first wall portion 34A, a second wall portion 36A, a second wall portion 36B, and a third wall portion 34B.

The press portion 32 of the press plate 30 has a rectangular shape in plan view, and is formed from a flat plate shaped member of uniform overall thickness. The press portion 32 configures a bottom wall of the press plate 30, and a lower face of the press portion 32 is configured so as to compress the breast N of the examinee W downwards (towards the imaging face 20) from the top portion of the breast N.

The first wall portion 34A of the support body 33 is disposed with length direction along one edge portion (along the X direction) on the chest wall side of the press portion 32, and is a rectangular shaped plate shaped member standing up (in the Z direction) from the edge portion. The first wall portion 34A is disposed facing the chest wall of the examinee W, and configures a front wall that is capable of contacting the chest wall. The third wall portion 34B faces the first wall portion 34A across a separation, and is disposed with length direction along another edge portion (along the X direction) on the opposite side (back face side) of the press portion 32 to the chest wall, and is a rectangular shaped plate shaped member standing up from the edge portion. The third wall portion 34B configures a rear wall.

The second wall portions 36A, 36B are integrally configured at both ends of the first wall portion 34A, and extend towards the back face side (in the Y direction) along other edge portions of the press portion 32 facing each other from the two sides. The second wall portions 36A, 36B are rectangular shaped plate shaped members standing up from the other edge portions. The second wall portion 36A is configured as a side wall on the left side, and the second wall portion 36B is configured as a side wall on the right side, as seen by the examinee W.

In the present exemplary embodiment, the press portion 32, the first wall portion 34A, the second wall portions 36A, 36B, and the third wall portion 34B are fabricated from similar materials to each other, and are for example fabricated from a resin material. Specifically, such resin materials include thermoplastic plastics, and more preferably employ a polycarbonate (PC) that can obtain such physical properties as high impact resistance properties, heat resistance properties, and fire-retardant properties. The press portion 32 is configured to be transparent such that the breast N can be seen in a compressed state. Resin materials that may be employed include for example polyethylene terephthalate (PET), acrylics, and polypropylene (PP). Although there is no particular limitation thereto, the press portion 32 is set with an X direction edge length of 240 mm to 300 mm, a Y direction edge length of 180 mm to 240 mm, and a Z direction thickness of 2.2 mm to 2.6 mm respectively. The first wall portion 34A, the second wall portions 36A, 36B, and the third wall portion 34B are respectively set with a Z direction height of 45 mm to 46 mm, and a Y direction or X direction thickness of 2.0 mm to 2.4 mm, so as to be slightly thinner than the thickness of the press portion 32.

The first wall portion 34A is slightly tilted towards the chest wall side about a connection location with the press portion 32. The tilt angle of the first wall portion 34A is set at for example 1 degree to 3 degrees with respect to a direction orthogonal to the press portion 32 (the Z axis), and is preferably set at 2 degrees. Moreover, in order to reduce the pain felt by the examinee W during the application of compression force, an outside surface configuring a corner portion between the press portion 32 and the first wall portion 34A is provided with a curved face. This curved face has a radius of curvature of for example 2 mm to 6 mm, and is preferably set at 4 mm. The second wall portions 36A, 36B are respectively slightly tilted towards the outside about connection locations with the press portion 32. The respective tilt angles of the second wall portions 36A, 36B are slightly larger than the tilt angle of the first wall portion 34A, and are for example set at 3 degrees to 5 degrees with respect to a direction orthogonal to the press portion 32, and are preferably set at 4 degrees. An outside surface configuring a corner portion between the press portion 32 and the second wall portion 36A, and an outside surface configuring a corner portion between the press portion 32 and the second wall portion 36B are respectively provided with curved faces, with these curved faces having a radius of curvature similar to the radius of curvature described above. The third wall portion 34B is set with a similar tilt angle to the respective second wall portions 36A, 36B. A corner portion between the press portion 32 and the third wall portion 34B is provided with a curved face with a similar radius of curvature to the curved face provided to the corner portion between the press portion 32 and the first wall portion 34A.

Slit Configuration

The first wall portion 34A is provided with a first slit 40 that is disposed with length direction running along the edge portion (along the X direction), and that is provided penetrating the first wall portion 34A from an outer wall face towards an inner wall face. The second wall portion 36A is moreover provided with a second slit 42A that is disposed with length direction running along the edge portion (along the Y direction) and that is provided penetrating the second wall portion 36A from an outer wall face towards an inner wall face. The second wall portion 36B is similarly provided with a second slit 42B that is disposed with length direction running along the edge portion (along the Y direction) and that is provided penetrating the second wall portion 36B from an outer wall face towards an inner wall face. The first slit 40 and the second slits 42A, 42B configure a deflection amount increasing component, described later.

In the present exemplary embodiment, a single first slit 40 is disposed in the first wall portion 34A. The width of the first slit 40 in the first wall portion 34A vertical direction (in the Z direction) is set wider than the width of the second slits 42A, 42B along the same direction. Although there is no particular limitation to these values, the width of the first slit 40 is for example set at 8 mm to 12 mm, and is preferably set at 10 mm. A single second slit 42A is disposed in the second wall portion 36A, and a single second slit 42B is disposed to the second wall portion 36B at a position facing the second slit 42A. Although there is no particular limitation to these values, the widths of the second slits 42A, 42B are for example respectively set at 4 mm to 8 mm, and are preferably set at 6 mm.

The first slit 40 is provided above the second slits 42A, 42B with respect to an upper face of the press portion 32. In other words, the second slit 42A is disposed at a location on the second wall portion 36A that is close to the press portion 32, with an attachment location 48A for the support arm 34 provided at a location above the second slit 42A. The attachment location 48A is provided with attachment holes 34J that penetrate from the outer wall face towards the inner wall face of the second wall portion 36A at a separation from each other in the Y direction. The second wall portion 36B is similarly provided with an attachment location 48B for the support arm 34 at a location above the second slit 42B. The attachment location 48A is provided with attachment holes 34K. Note that a separation distance between the first slit 40 and the second slits 42A, 42B is set at 6 mm to 10 mm, and is preferably set at 8 mm.

The press plate 30 is formed with a corner portion 38A at the boundary between the first wall portion 34A and the second wall portion 36A, and is also formed with a corner portion 38B at the boundary between the first wall portion 34A and the second wall portion 36B. A corner portion 38C is moreover formed at the boundary between the third wall portion 34B and the second wall portion 36B, and a corner portion 38D is formed at the boundary between the third wall portion 34B and the second wall portion 36A. In the present exemplary embodiment, outer wall faces and inner wall faces of the corner portions 38A to 38D are respectively configured as curved faces. Although there is no particular limitation to these values, the outer wall faces of the corner portions 38A to 38D have a radius of curvature set at for example 12 mm to 18 mm, and is preferably set at 15 mm. Note that there is no limitation to curved faces for the corner portions 38A to 38D, and configuration may be made with right-angled profiles or beveled profiles.

Corner Portion Slit Configuration

The corner portion 38A of the press plate 30 is provided with a first corner portion slit 44A that is provided straddling the corner portion 38A, that penetrates the corner portion 38A, that is connected to the first slit 40, and that is disposed at a separation to the second slit 42A. The first corner portion slit 44A is configured so as to extend the first slit 40 to the corner portion 38A. The direction and the dimension of the width of the first corner portion slit 44A is set the same as the direction and the dimension of the width of the first slit 40. A terminal end of the first corner portion slit 44A in the second wall portion 36A is configured with a circular arc shape as seen in side view of the second wall portion 36A, reducing stress concentration at this location. The corner portion 38B is similarly provided with a first corner portion slit 44B that is provided straddling the corner portion 38B, that penetrates the corner portion 38B, that is connected to the first slit 40, and that is disposed at a separation to the second slit 42B.

The corner portion 38A is provided with a second corner portion slit 46A that is provided straddling the corner portion 38A, that penetrates the corner portion 38A, that is connected to the second slit 42A, and that is disposed at a separation to the first slit 40. The second corner portion slit 46A is configured so as to extend the second slit 42A to the corner portion 38A. The direction and the dimension of the width of the second corner portion slit 46A is set the same as the direction and the dimension of the width of the second slit 42A. The second corner portion slit 46A is disposed at a Z direction separation to and parallel to the first corner portion slit 44A at the corner portion 38A. Namely the first corner portion slit 44A that is connected to the first slit 40 and the second corner portion slit 46A that is connected to the second slit 42A are configured so as to pile up in the Z direction at the corner portion 38A. A terminal end of the second corner portion slit 46A in the first wall portion 34A is configured with a circular arc shape in face-on view of the first wall portion 34A, reducing stress concentration at this location. The corner portion 38B is similarly provided with a second corner portion slit 46B that is provided straddling the corner portion 38B, that penetrates the corner portion 38B, that is connected to the second slit 42B, and that is disposed at a separation to the first slit 40. The second corner portion slit 46B is disposed at a separation to and parallel to the first corner portion slit 44B at the corner portion 38B. Namely, the first corner portion slit 44B that is connected to the first slit 40 and the second corner portion slit 46B that is connected to the second slit 42B are configured so as to pile up at the corner portion 38B. The first corner portion slits 44A, 44B and the second corner portion slits 46A, 46B configure the deflection amount increasing component together with the first slit 40 and the second slits 42A, 42B.

Reinforcement Member Configuration

As illustrated in FIG. 3, FIG. 4, FIG. 6, FIG. 8, and FIG. 12A to FIG. 12C, the press plate 30 is provided with a reinforcement member 50 at an inner wall face above the first slit 40 of the first wall portion 34A. The reinforcement member 50 is formed from a material that is harder than the material of the support body 33. The reinforcement member 50 includes a reinforcement member main body 50A that is disposed with length direction along the X direction and has a long thin rectangular plate shape, and a bead portion 50B that is disposed along the reinforcement member main body 50A length direction at a central portion of the reinforcement member main body 50A, and that projects out towards the press plate 30 inside. The bead portion 50B raises the mechanical rigidity of the reinforcement member main body 50A. There are no particular limitations to the reinforcement member main body 50A, however for example an austenitic stainless steel (SUS304) plate material with excellent corrosion resistance, toughness, ductility and workability may be employed. The Z direction width of the reinforcement member main body 50A is for example set at 12 mm to 16 mm, and is preferably set at 14 mm. The plate thickness of the reinforcement member main body 50A is for example set at 1 mm to 2 mm, and is preferably set at 1.5 mm. Note that the reinforcement member 50 may be provided above the first slit 40 on the outer wall face of the first wall portion 34A. In the present example, length direction end portions of the reinforcement member 50 are configured within the first wall portion 34A, however configuration may be made wherein the length direction end portions of the reinforcement member 50 are extended so as to straddle the corner portion 38A and the corner portion 38B, thereby raising the rigidity at the corner portion 38A and the corner portion 38B.

Gap Member Configuration

As illustrated in FIG. 2 and FIG. 13A to FIG. 13C, the press plate 30 is provided with a gap member 60 inside the first slit 40, the first corner portion slit 44A, and the first corner portion slit 44B. The gap member 60 is formed from a material that is softer than the material of the support body 33. The gap member 60 is integrally formed with a gap member 60A provided to the first slit 40, and a gap member 60B that is provided to the first corner portion slit 44A, thus configuring an L-shape in plan view as illustrated in FIG. 13B. The gap member 60 is similarly integrally formed with a gap member 60C that is provided to the first corner portion slit 44B and that is integrally formed to the gap member 60A, thus configuring an L-shape in plan view. As illustrated in FIG. 13B and FIG. 13C, the widths of locations in the gap member 60 that respectively project out slightly towards the outer wall face side and the inner wall face side of the first wall portion 34A, the corner portion 38A and the corner portion 38B are set larger than the width of a thickness direction central portion provided inside the first slit 40. The gap member 60 employs a material that does not respectively impede deformation of the gap member 60 due to compression force or reaction force at a location between the first slit 40 and the press portion 32, and at a location between the first corner portion slits 44A, 44B and the press portion 32. For example, a contractible or resilient elastomer (rubber material) is employed for the gap member 60.

The gap members 60B, 60C provided to the first corner portion slits 44A, 44B are each configured with a similar thickness to the gap member 60A, however are of higher rigidity than the gap member 60A provided to the first slit 40 due to the difference in the moment of inertia of area thereto. Note that the gap members 60B, 60C may be configured with a greater thickness than the thickness of the gap member 60A to provide even higher rigidity. Moreover, the gap members 60B, 60C may be set with greater hardness than the hardness of the gap member 60A to provide even higher rigidity.

Figure 14A:
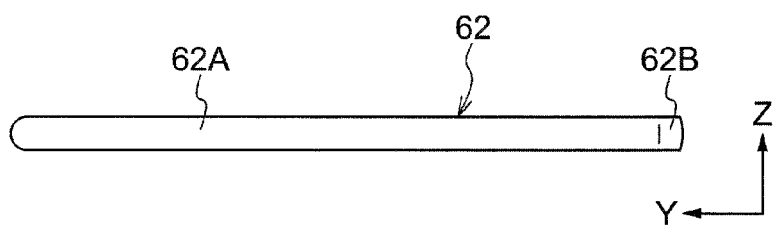
FIG. 14A is a front face view of a gap member provided to a second slit and a second corner portion slit of the press plate illustrated in FIG. 2.
Figure 14C:
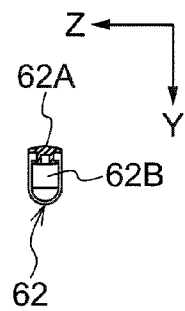
FIG. 14C is a cross-section illustrating the gap member illustrated in FIG. 14B, taken along line 14C-14C and viewed from the direction indicated by the arrows.
Figure 14B:
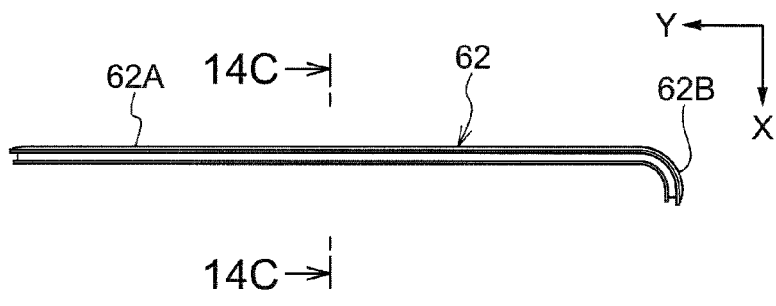
FIG. 14B is a plan view of the gap member illustrated in FIG. 14A.
Figure 14D:
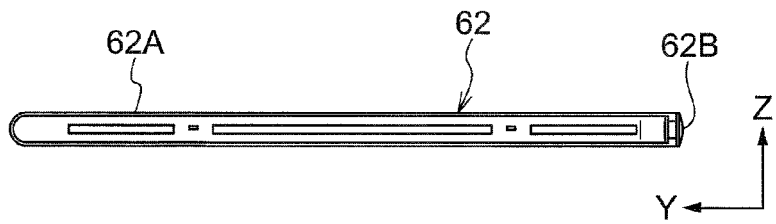
FIG. 14D is a back face view of the gap member illustrated in FIG. 14A.

As illustrated in FIG. 2 and FIG. 14A to 14D, the press plate 30 is provided with a gap member 62 that is similar to the gap member 60 inside the second slit 42A and the second corner portion slit 46A. The gap member 62 is integrally formed with a gap member 62A provided to the second slit 42A and a gap member 62B provided to the second corner portion slit 46A, thus configuring an L-shape in plan view as illustrated in FIG. 14B. A similar gap member 62 is also provided in the second slit 42B and the second corner portion slit 46B. The gap member 62 employs a material similar to the material of the gap member 60. The gap member 62B provided to the second corner portion slits 46A, 46B is moreover set with higher rigidity than that of the gap member 62A provided to the second slits 42A, 42B.

Support Arm Configuration

As illustrated in FIG. 1, FIG. 2, FIG. 9 and FIG. 10, the support arm 34 is provided with a plate shaped back face arm portion 35A that extends along the X direction facing the third wall portion 34B of the press plate 30, and a pair of plate shaped side face arm portions 35B, 35C that extend facing each other from both ends of the back face arm portion 35A towards the chest wall side (the opposite side to the Y direction). The side face arm portions 35B, 35C are integrally formed to the first wall portion 34A in the present example, and are configured by bending the back face arm portion 35A towards the chest wall side at both ends. Although there is no particular limitation thereto, an aluminum alloy material with medium strength and excellent corrosion resistance, more specifically an Al—Mg alloy material, is employed for the support arm 34.

Figure 2:
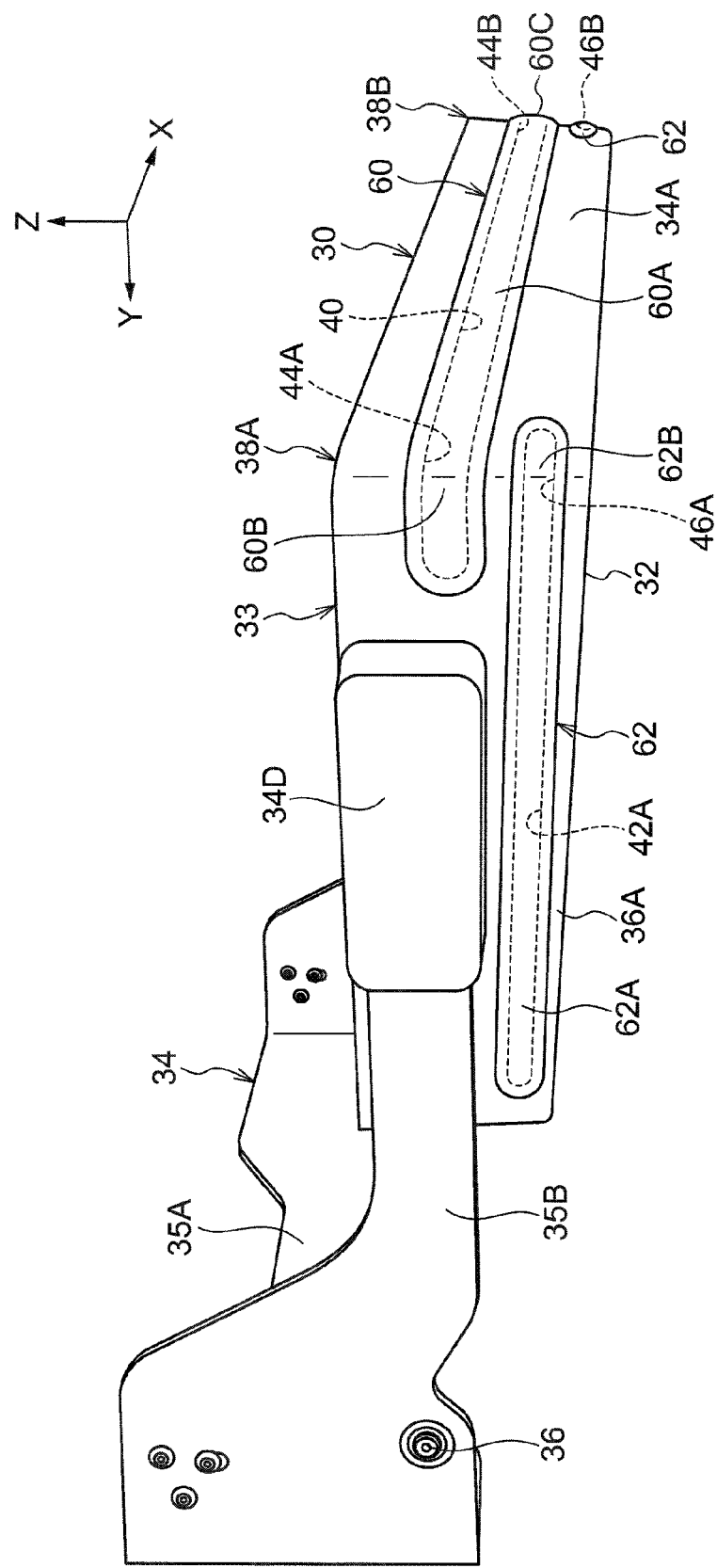
FIG. 2 is a perspective view illustrating a press plate and a support arm provided to a radiographic imaging apparatus according to the first exemplary embodiment, as viewed from the origin side of XYZ coordinate axes.
Figure 3:
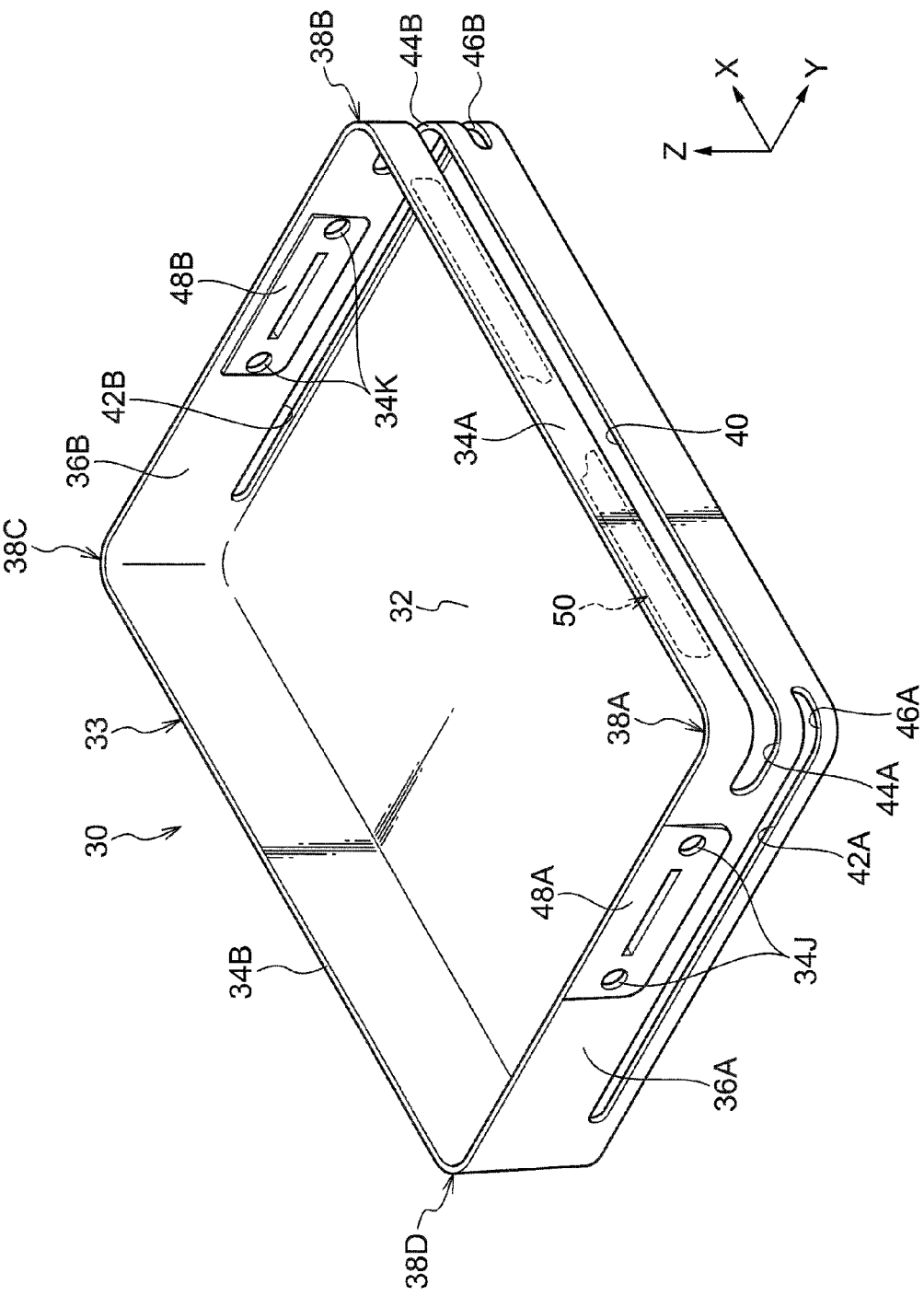
FIG. 3 is a perspective view of the press plate illustrated in FIG. 2, as viewed from a Z direction upper side of the base point.
Figure 4:
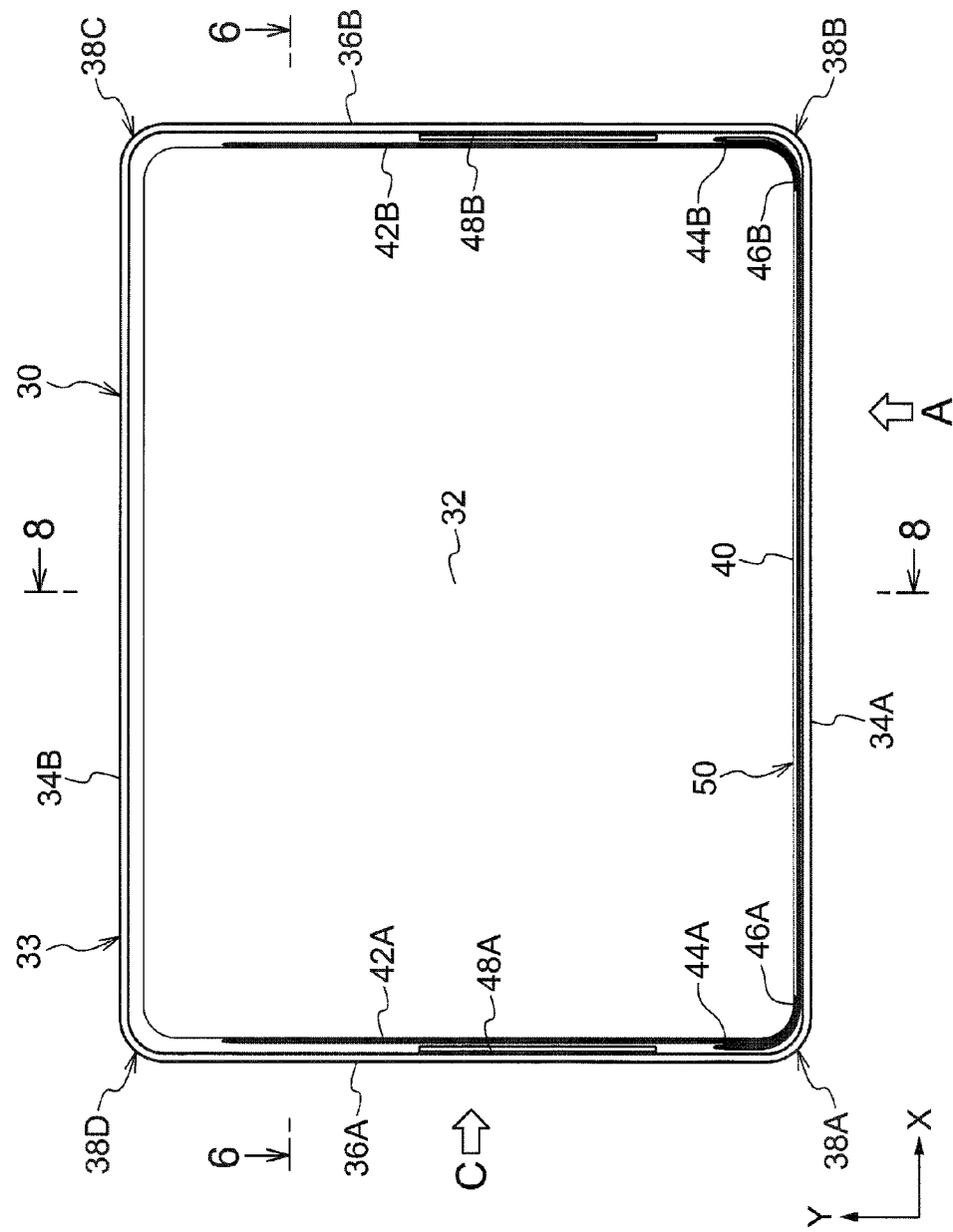
FIG. 4 is a plan view of the press plate illustrated in FIG. 3.
Figure 5:
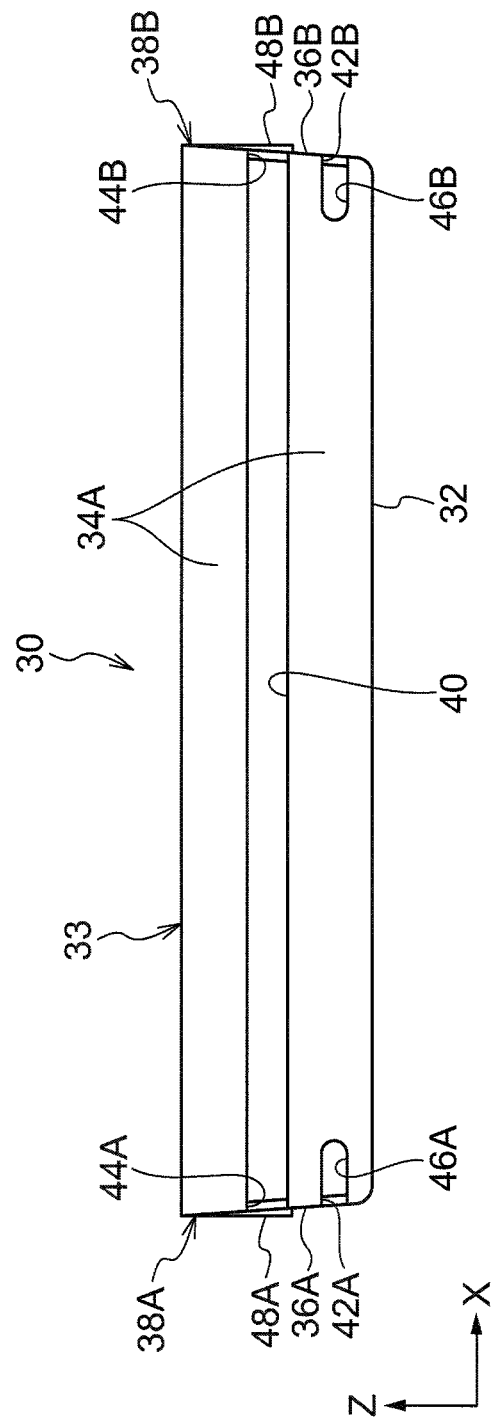
FIG. 5 is a front face view illustrating the press plate illustrated in FIG. 4, as viewed along the direction indicated by arrow A.
Figure 6:
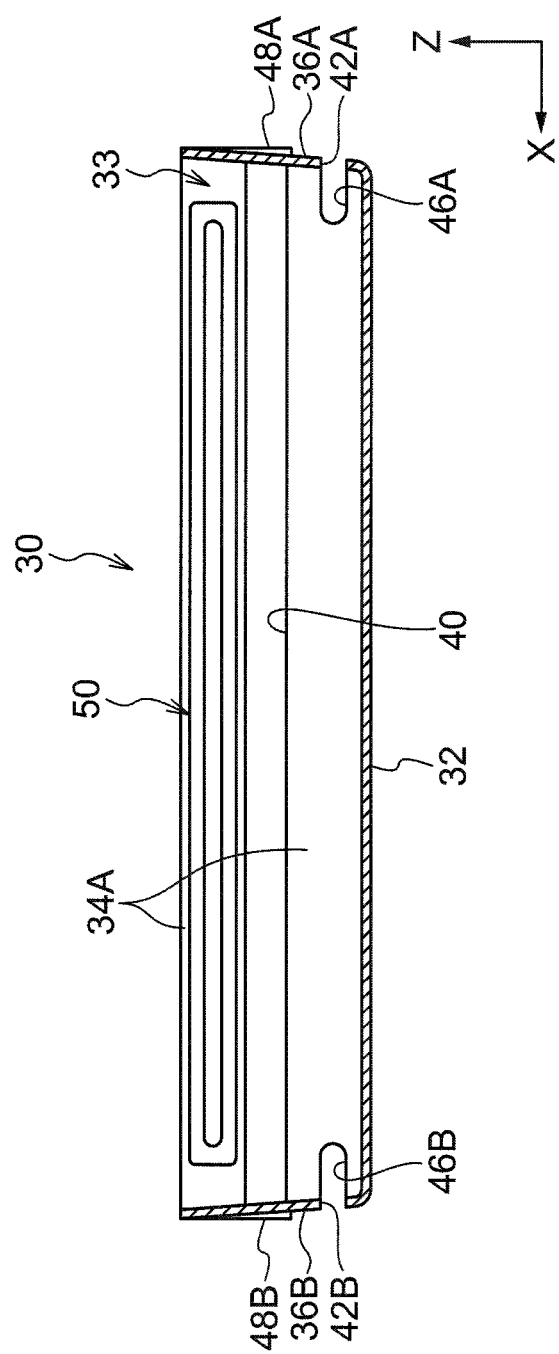
FIG. 6 is a cross-section illustrating the press plate illustrated in FIG. 4 taken along line 6-6, as viewed along the direction indicated by the arrows.
Figure 7:
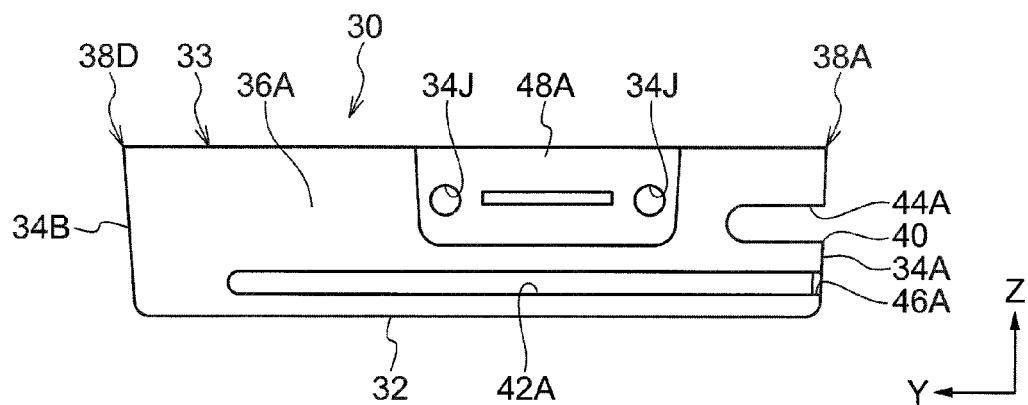
FIG. 7 is a side view illustrating the press plate illustrated in FIG. 4, as viewed along the direction indicated by arrow C.
Figure 8:
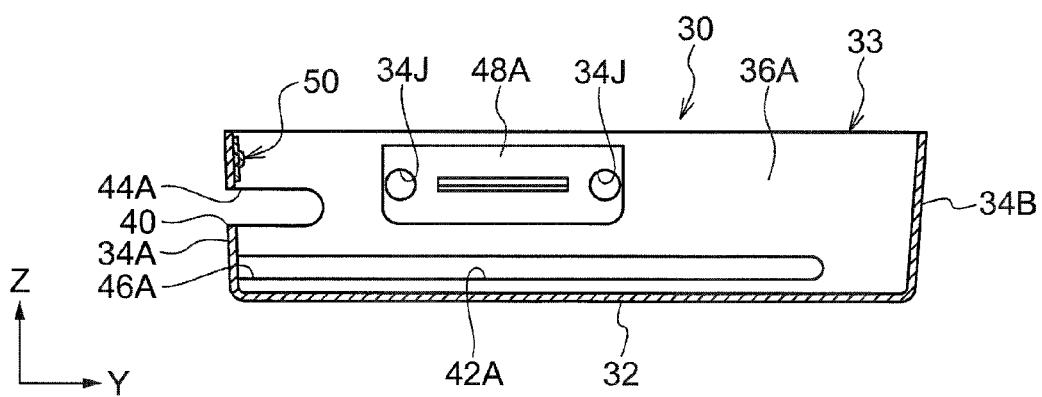
FIG. 8 is a cross-section illustrating the press plate illustrated in FIG. 4 taken along line 8-8, as viewed along the direction indicated by the arrows.
Figure 9:
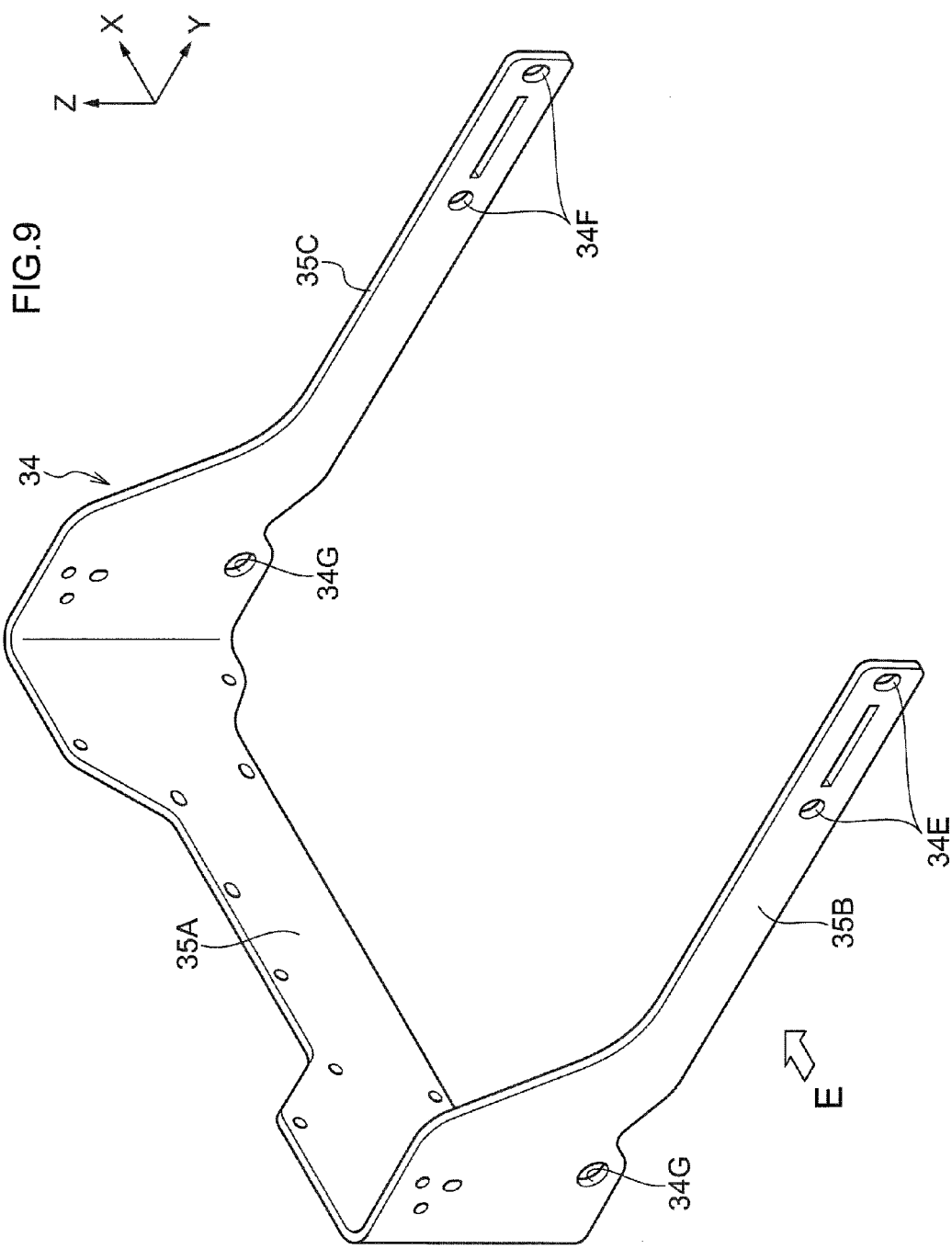
FIG. 9 is a perspective view illustrating the support arm illustrated in FIG. 2, as viewed from the same position as FIG. 3.
Figure 10:
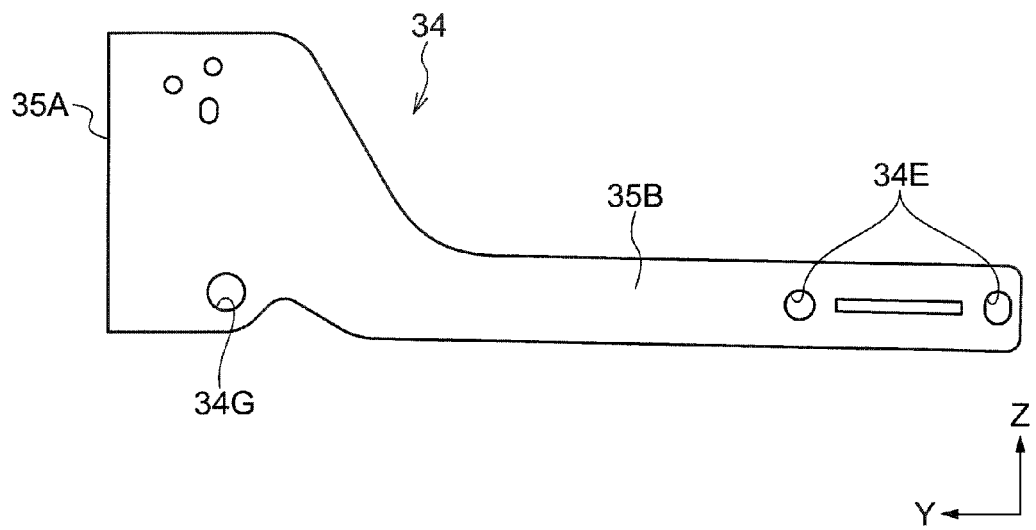
FIG. 10 is a side view illustrating the support arm illustrated in FIG. 9, as viewed along the direction illustrated by the arrow F.

As illustrated in FIG. 9 and FIG. 10, rotation shaft holes 34G are provided penetrating the side face arm portions 35B, 35C on the back face arm portion 35A side. The rotation shaft holes 34G are provided with the rotation shaft 36 illustrated in FIG. 1 and FIG. 2. Attachment holes 34E are provided on the chest wall side of the side face arm 34B. The attachment holes 34E are in communication with the attachment holes 34J provided to the attachment location 48A of the press plate 30 illustrated for example in FIG. 3, and the second wall portion 36A of the press plate 30 is attached to the side face arm 34B through the attachment holes 34E, 34J. Attachment holes 34F are similarly provided on the chest wall side of the side face arm 34C for support. The attachment holes 34F are in communication with the attachment holes 34K provided to the attachment location 48B of the press plate 30, and the second wall portion 36B of the press plate 30 is attached to and supported by the side face arm 34C through the attachment holes 34F, 34K. Such a configuration enables adjustment of the angle of the press portion 32 with respect to the imaging face 20 about the rotation shaft 36 through the support arm 34 in the press plate 30. Note that an attachment cover 34D illustrated in FIG. 2 is attached so as to cover the attachment location 48B from the outside.

Support Base Member Configuration

Figure 11:
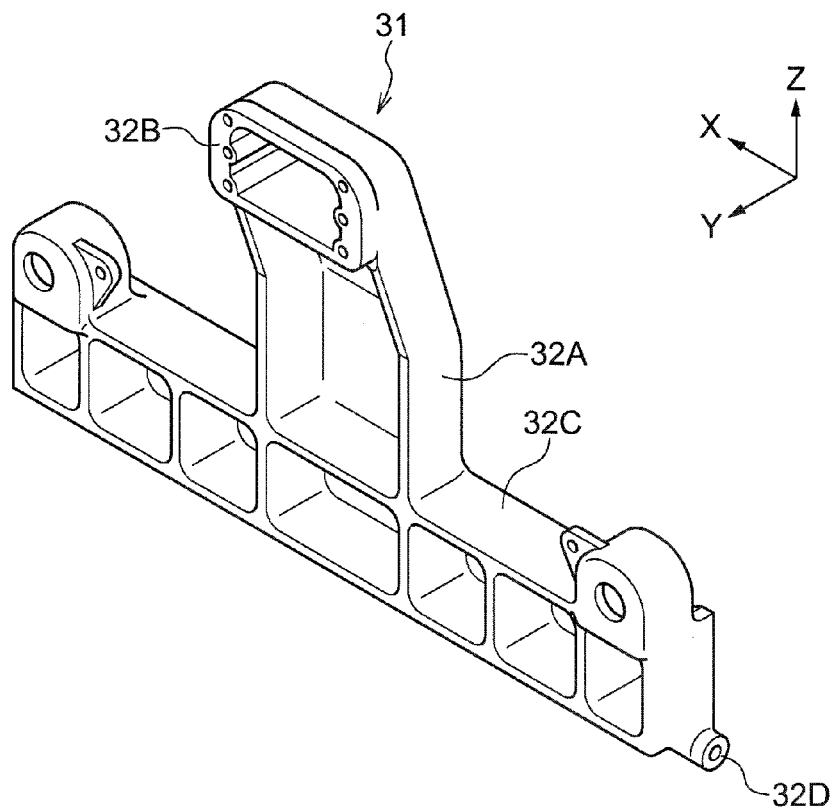
FIG. 11 is a perspective view illustrating a support base member that supports the support arm illustrated in FIG. 9 and FIG. 10, as viewed from a back face side.

As illustrated in FIG. 1 and FIG. 11, the support base member 31 includes an attachment portion 32B that is attached to the holder 24, an extension portion 32A that is configured integrally to the attachment portion 32B and that extends towards the lower side, and an arm support portion 32C that is configured integrally to a lower end of the extension portion 32A and extends to both ends of the extension portion 32A. The extension direction of the arm support portion 32C matches the extension direction of the back face arm portion 35A of the support arm 34. An attachment structure is configured such that the back face arm portion 35A of the support arm 34 is attached to the arm support portion 32C by a fastening component such as by screws or by nuts and bolts. The support base member 31 is a block body provided with rib portions and with a reduced thickness to give a lightweight configuration of the support base member 31. Although there is no particular limitation thereto, for example an aluminum alloy material with excellent mechanical properties, machinability and casting properties, specifically an Al—Si—Cu alloy material, is employed for the support base member 31.

Press Plate Operation

In the press plate 30 according to the present exemplary embodiment, the breast N of the examinee W is interposed between the imaging face 20 of the imaging table 22 illustrated in FIG. 1 and the press plate 30 illustrated in for example FIG. 2, and the breast N is compressed from an top portion of the breast N by the press portion 32 of the press plate 30.

Figure 15:
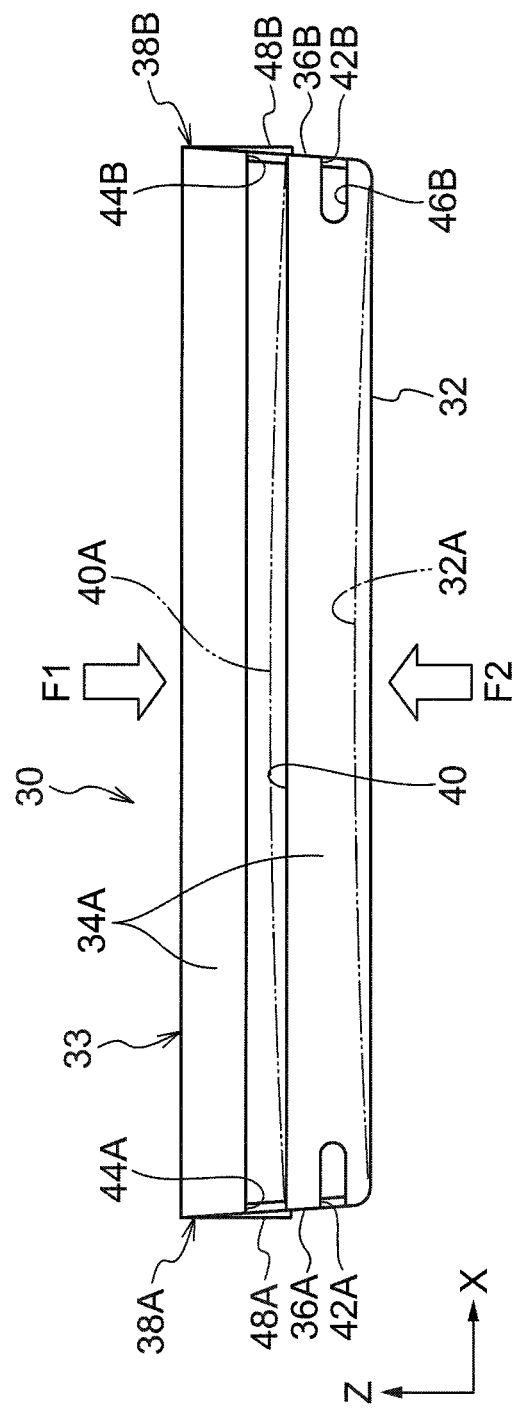
FIG. 15 is a front face view of a press plate corresponding to FIG. 5, illustrating a state in which a compression force and a reaction force are being applied.

As illustrated in FIG. 15, a downwards compression force F1 applied from the support arm 34 to the support body 33 is transmitted to the press portion 32, and the press portion 32 compresses the breast N according to the compression force F1. When this compression force F1 is applied to the breast N, a reaction force F2 pushing the press portion 32 in an upwards direction arises in the breast N. In the chest wall side first wall portion 34A of the press plate 30, the rigidity is reduced at a location between the first slit 40 and the press portion 32 due to providing the first slit 40, and deflection of the press portion 32 due to the reaction force F2 occurs as shown by the double-dotted dashed line labeled 32A. In the present example, when an axial center portion of the breast N is positioned at an X direction intermediate portion of the first wall portion 34A, the deflection amount due to the reaction force F2 is greatest at this intermediate portion. The double-dotted dashed line labeled 40A illustrates a deformed state of the first slit 40 towards the press portion 32 side.

Figure 16:
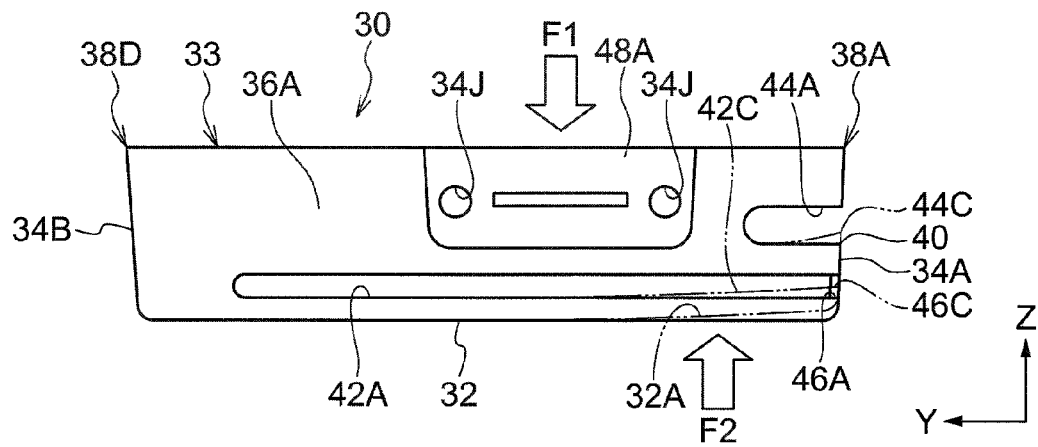
FIG. 16 is a side view of a press plate corresponding to FIG. 7, illustrating a state in which a compression force and a reaction force are being applied.

As illustrated in FIG. 16, rigidity is reduced at a location between the second slit 42A and the press portion 32 due to providing the second slit 42A to the second wall portion 36A on the chest wall side face side of the press plate 30. Deflection of the press portion 32 occurs due to the reaction force F2 as shown by the double-dotted dashed line labeled 32A. The deflection amount due to the reaction force F2 is greatest on the chest wall side of the second wall portion 36A. The double-dotted dashed line labeled 42C illustrates a deformed state of the second slit 42A on the press portion 32 side. On the second wall portion 36B side similar deflection occurs in the press portion 32 and the second slit 42B due to providing the second slit 42B.

Figure 17:
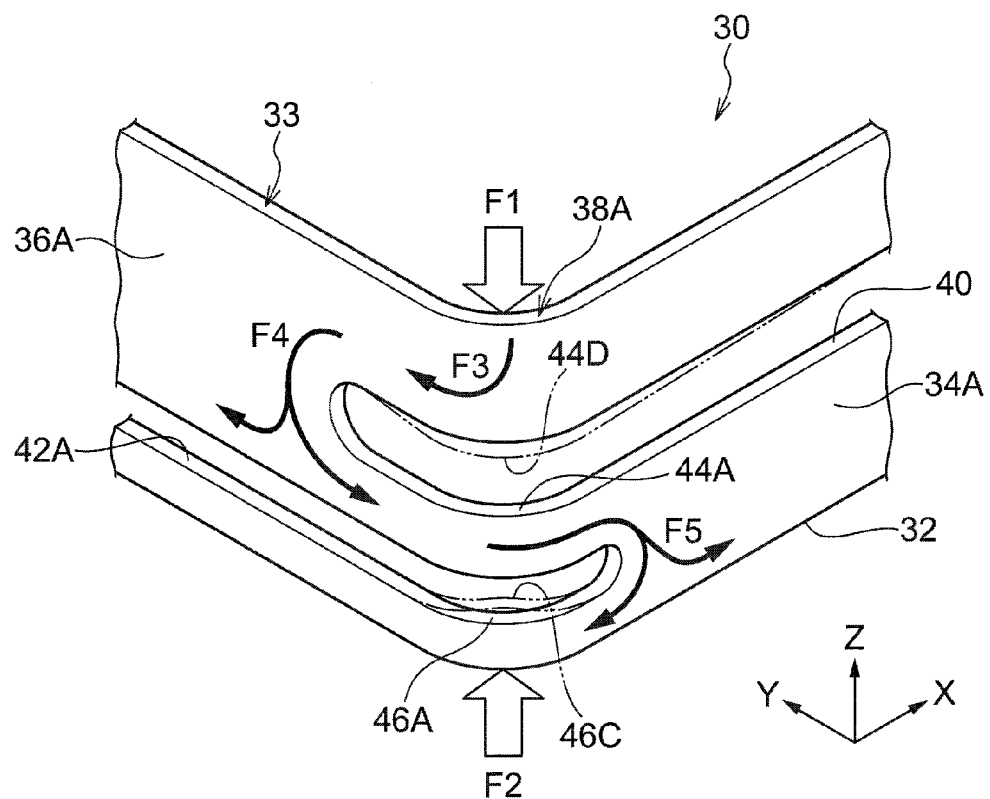
FIG. 17 is a perspective view of a corner portion of a press plate, illustrating a state in which a compression force and a reaction force are being applied.

As illustrated in FIG. 17, rigidity is reduced at a location (separation location) between the first corner portion slit 44A and the second corner portion slit 46A due to providing the first corner portion slit 44A to the corner portion 38A of the press plate 30. Rigidity is moreover reduced at a location between the first corner portion slit 44A and an upper end of the corner portion 38A. Since the first corner portion slit 44A is connected to the first slit 40, rigidity is also reduced at upper and lower locations of the connection location. Rigidity is moreover reduced at a location between the second corner portion slit 46A and the press portion 32 due to providing the second corner portion slit 46A to the corner portion 38A. Since the second corner portion slit 46A is connected to the second slit 42A, rigidity is similarly reduced at upper and lower locations of this connection location.

When the compression force F1 is applied to the upper end of the corner portion 38A, deformation occurs in the first corner portion slit 44A as illustrated by the double-dotted dashed line labeled 44D, and the compression force F1 at the corner portion 38A circumnavigates the first corner portion slit 44A as compression forces F3, F4 and is dispersed. The compression force F4 is transmitted to the separation location between the first corner portion slit 44A and the second corner portion slit 46A, and is dispersed by circumnavigating the second corner portion slit 46A whilst being transmitted to the press portion 32 as a compression force F5. The reaction force F2 from the breast N arises in the press portion 32 according to the compression force F5 transmitted to the press portion 32. Deflection occurs in the press portion 32 as illustrated by the double-dotted dashed line labeled 46C due to the reaction force F2.

At the corner portion 38A, upper and lower locations separated by the first corner portion slit 44A of the support body 33 circumvent the first corner portion slit 44A at the second wall portion 36A, and are coupled together at the separation location between the first corner portion slit 44A and the second slit 42A. Similarly, at the corner portion 38A, upper and lower locations separated by the second corner portion slit 46A of the support body 33 circumvent the second corner portion slit 46A at the first wall portion 34A and are coupled at the separation locations of the second corner portion slit 46A and the first slit 40. The side view profile of a support location at the corner portion 38A is accordingly configured with an S-shaped profile or a crank-shaped meandering profile from the upper end of the support body 33 to the lower end of the press portion 32.

EXAMPLE

Actual deflection amounts of the press portion 32 due to the reaction force F2 are measured for the press plate 30 of the first exemplary embodiment. Example 1 to Example 6 below give actual measured deflection amount values that are measured under varying conditions, and are explained whilst making comparisons to a Comparative Example 1 to a Comparative Example 6.

Example 1 and Comparative Example 1

Figure 18A:
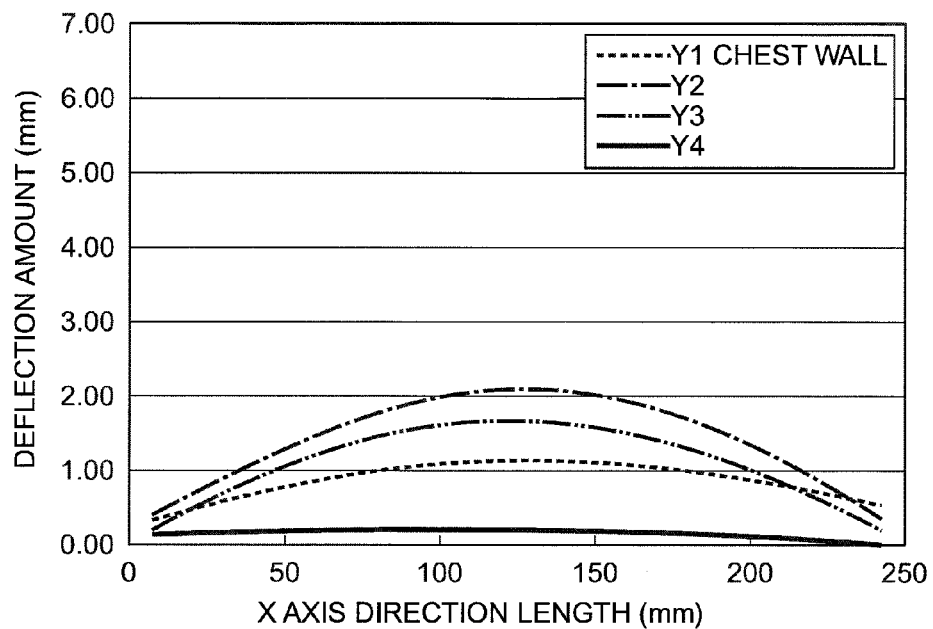
FIG. 18A is a graph illustrating a relationship between X axis direction length (at a chest wall side position) and deflection amount in a press portion of a press plate according to an Example 1 of the first exemplary embodiment.

FIG. 18A illustrates a relationship between a deflection amount in mm of the press portion 32 and positions (X direction positions) in mm from a coordinate origin at an edge portion of the press portion 32 where the first wall portion 34A stands up in a press plate 30 according to Example 1. The press portion 32 is set with an X direction length of 250 mm and a Y direction length of 180 mm. Data Y1 shows the deflection amount at a chest wall side Y direction 8 mm position, data Y2 shows the deflection amount at a Y direction 64 mm position, data Y3 shows the deflection amount at a Y direction 120 mm position, and data Y4 shows the deflection amount at a Y direction 178 mm position. The weight used in measuring the deflection amount has a weight of 33N (3.4 kgf). Since 60N to 80N are normally employed during radiographic imaging of the breast N, Example 1 gives measurement results for a small compression force F1. A Y direction contact range of the press portion 32 is configured with standard values of 80 mm to 120 mm.

As illustrated in FIG. 18A, for an X direction intermediate portion of the press portion 32, a maximum deflection amount of the press plate 30 in excess of 2.0 mm is measured in the region of 64 mm to 120 mm in the Y direction. At the X direction intermediate portion of the press portion 32, a deflection amount of about half the maximum deflection amount is measured at the Y direction 8 mm (data Y1) position. For both X position ends of the press portion 32 (at 8 mm and 242 mm in the X direction), a deflection amount in excess of zero is measured for a Y direction range of 8 mm to 120 mm.

Figure 22:
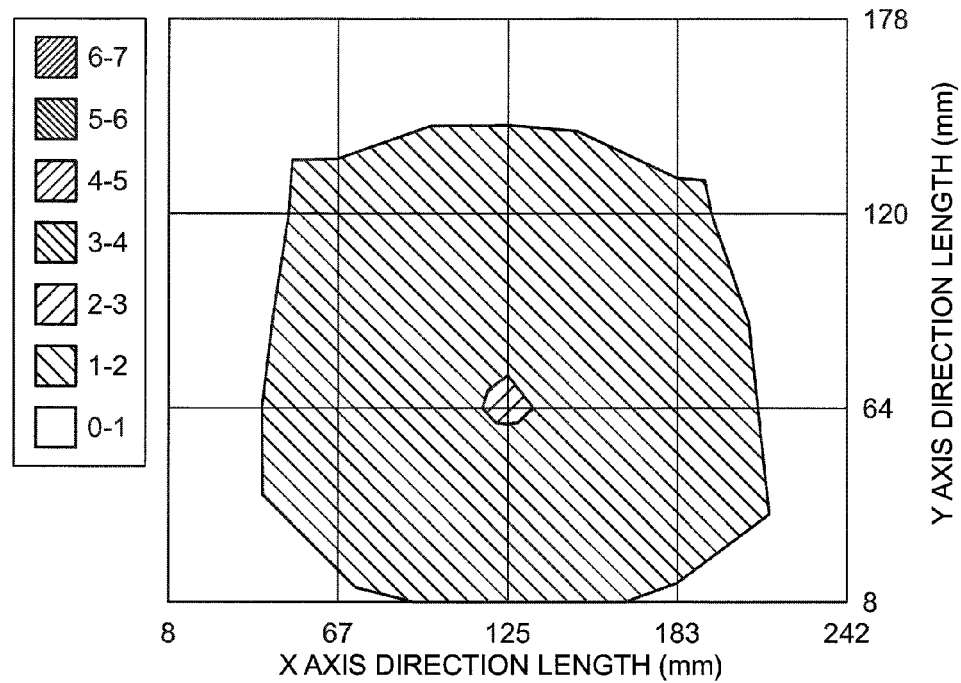
FIG. 22A is a deflection amount distribution diagram of the press portion according to Example 1.
FIG. 22B is a deflection amount distribution diagram of the press portion according to Comparative Example 1.
Figure 22:
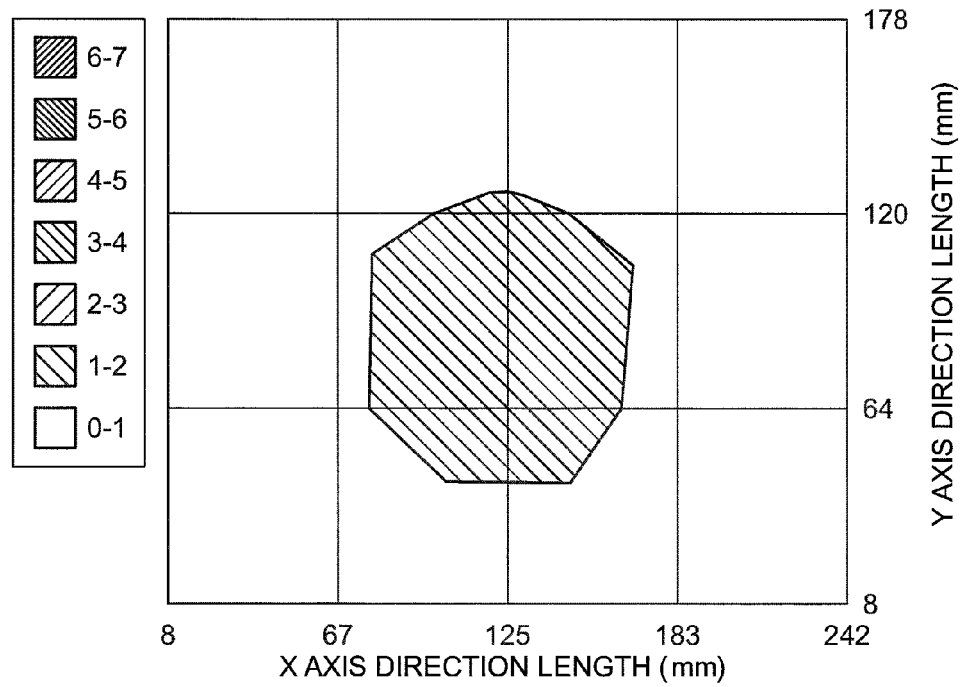

FIG. 22A is a press portion 32 deflection amount distribution diagram for the press plate 30 of the first exemplary embodiment. As illustrated in FIG. 22A, it can be confirmed that deflection occurs up to a Y direction position of 8 mm (data Y1), namely that deflection occurs up to the chest wall side.

Figure 18B:
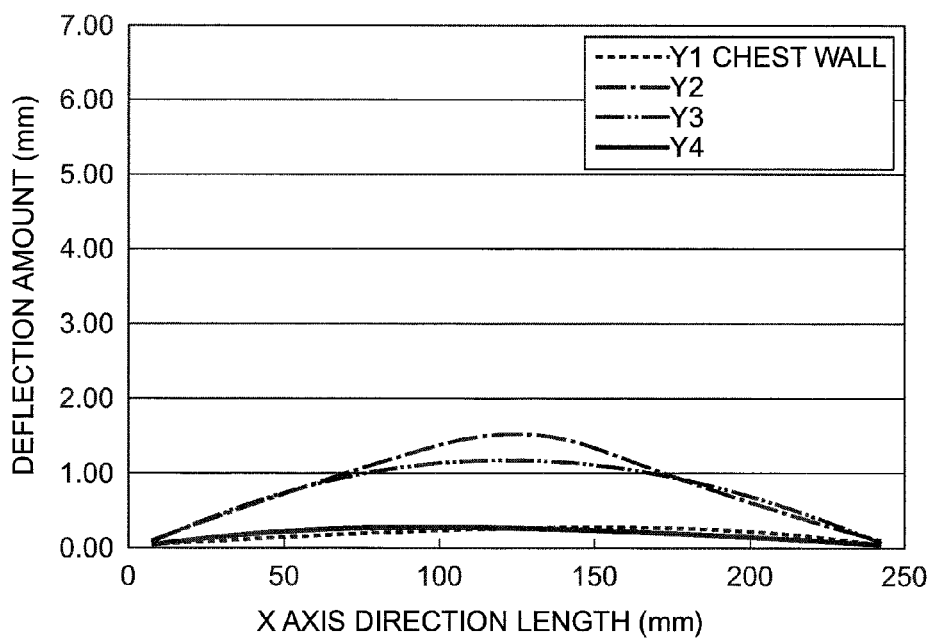
FIG. 18B is a graph illustrating a relationship between X axis direction length and deflection amount in a press portion of a press plate according to a Comparative Example 1.

FIG. 18B illustrates deflection amounts of a press plate according to Comparative Example 1. The press plate of Comparative Example 1 is not provided with the first slit 40, the second slits 42A, 42B, the first corner portion slits 44A, 44B or the second corner portion slits 46A, 46B of the press plate 30 of Example 1. Measurement conditions are the same. In the press plate of Comparative Example 1, the overall deflection amount is smaller than that of the press plate 30 of Example 1. Moreover, a very small deflection amount is measured for an X direction intermediate portion of the press portion at a Y direction position of 8 mm (data Y1). However, at both X direction ends of the press portion (at 8 mm and 242 mm in the X direction), the deflection amount is zero in the Y direction range of 8 mm to 120 mm. Deflection cannot be confirmed at the chest wall side, as illustrated in the deflection amount distribution diagram of the press portion of the press plate according to Comparative Example 1 illustrated FIG. 22B.

Example 2 and Comparative Example 2

Figure 19A:
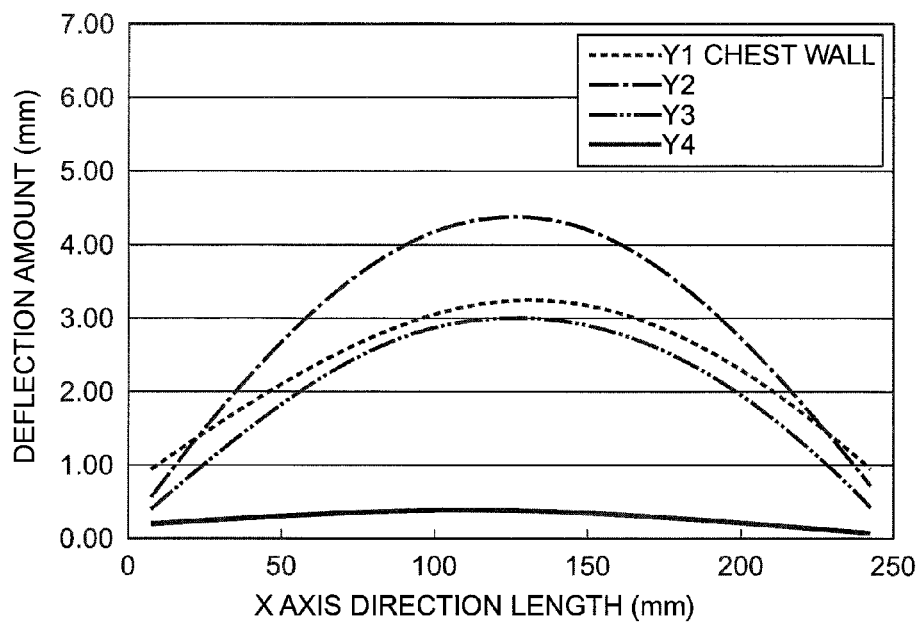
FIG. 19A is a graph illustrating a relationship between X axis direction length and deflection amount in a press portion of a press plate according to an Example 2 of the first exemplary embodiment.

FIG. 19A illustrates a relationship between a deflection amount in mm of the press portion 32 and positions in mm along an edge portion of the press portion 32 in a press plate 30 of Example 2. Note that the size and Y direction measurement positions of the press portion 32 are the same as in Example 1. The weight used in measuring the deflection amount has a weight of 78N (8.0 kgf). As illustrated in FIG. 19A, overall an increased deflection amount is measured in the press plate 30 according to the applied weight. The increasing deflection trend is similar to that of the press plate 30 of Example 1, however at the X direction intermediate portion of the press portion 32, a deflection amount of 72% to 74% of the maximum deflection amount is measured for the Y direction 8 mm (data Y1) position. Moreover, a deflection amount of nearly 1.0 mm is measured at both X direction ends (at 8 mm and 242 mm in the X direction), particularly at the Y direction 8 mm location, in the press portion 32.

Figure 23A:
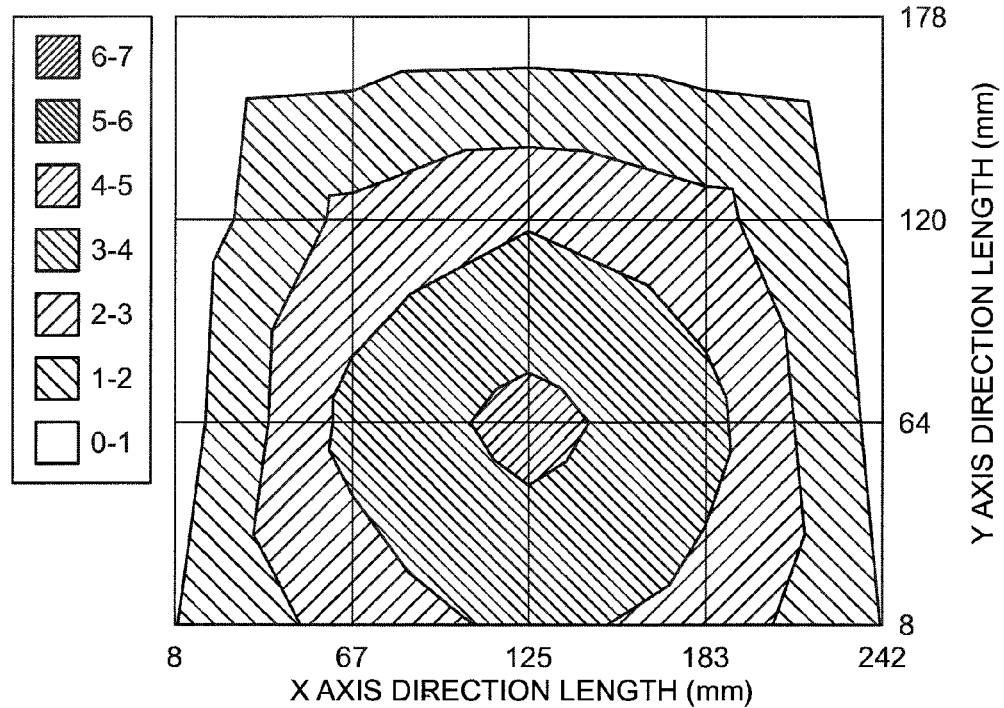
FIG. 23A is a deflection amount distribution diagram of the press portion according to Example 2.

FIG. 23A is a deflection amount distribution diagram for the press portion 32 of the press plate 30 according to Example 2. As illustrated in FIG. 23A, it can be confirmed that deflection occurs up to the Y direction 8 mm (data Y1) position, namely that deflection occurs up to the chest wall side. Deflection at both X direction ends (at 8 mm and 242 mm in the X direction) can also be confirmed.

Figure 19B:
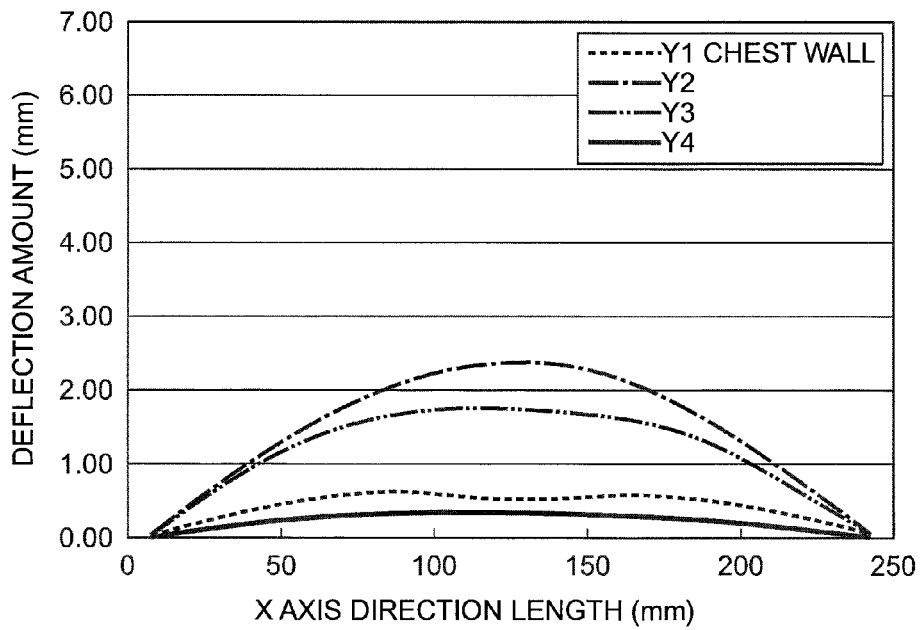
FIG. 19B is a graph illustrating a relationship between X axis direction length and deflection amount in a press portion of a press plate according to a Comparative Example 2.
Figure 23B:
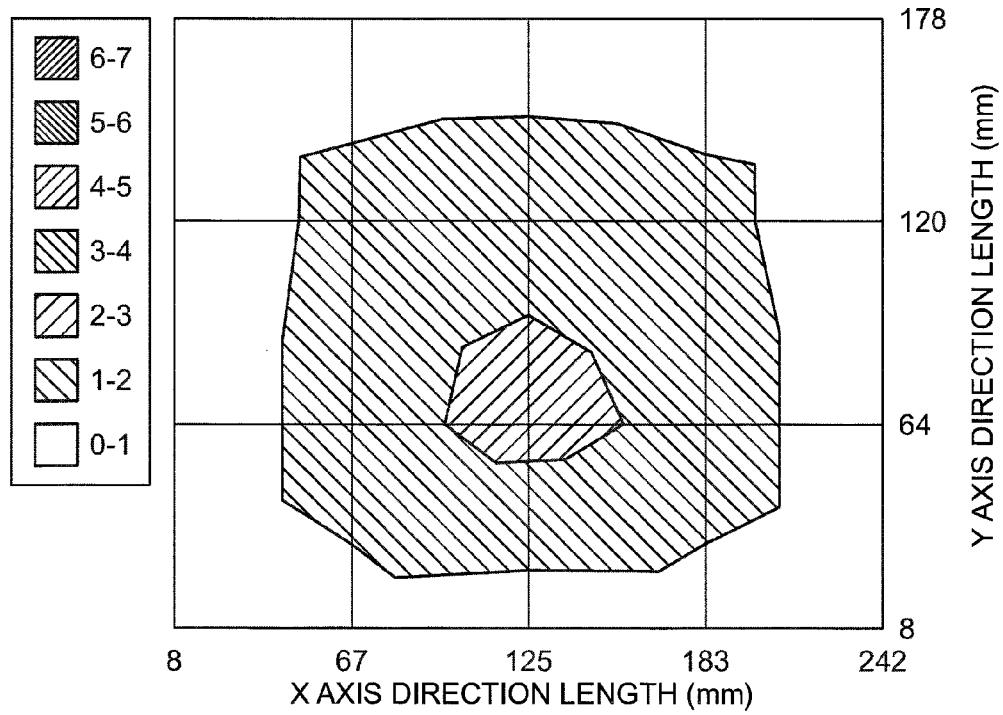
FIG. 23B is a deflection amount distribution diagram of the press portion according to Comparative Example 2.

However, as illustrated in FIG. 19B, in the press plate of Comparative Example 2, only a very small increase in deflection amount is measured under the same deflection amount measurement conditions as for the press plate 30 of Example 2. Similarly to the press plate of Comparative Example 1, the press plate of Comparative Example 2 has a deflection amount of zero at both X direction ends (at 8 mm and 242 mm in the X direction) of the press portion in a range of 8 mm to 120 mm along the Y direction. Deflection at the chest wall side cannot be confirmed, as illustrated in the deflection amount distribution diagram of the press portion of the press plate according to Comparative Example 2 illustrated FIG. 23B.

Example 3 and Comparative Example 3

Figure 20A:
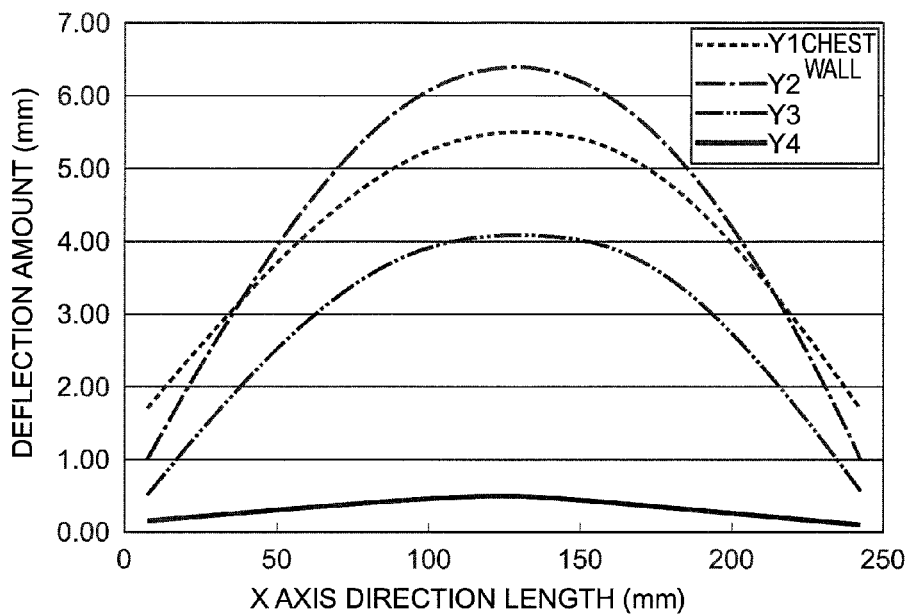
FIG. 20A is a graph illustrating a relationship between X axis direction length and deflection amount in a press portion of a press plate according to an Example 3 of the first exemplary embodiment.

FIG. 20A illustrates a relationship between a deflection amount in mm of the press portion 32 and positions in mm along an edge portion of the press portion 32 in a press plate 30 of Example 3. Note that the size and Y direction measurement positions of the press portion 32 are the same as in Example 1. The weight used in measuring the deflection amount has a weight of 123N (12.6 kgf). As illustrated in FIG. 20A, overall an increased deflection amount is measured in the press plate 30 according to the applied weight. The increasing deflection trend is similar to that of the press plates 30 of Example 1 and Example 2, however at the X direction intermediate portion of the press portion 32 a deflection amount of 86% to 88% of the maximum deflection amount is measured for the Y direction 8 mm (data Y1) position. Moreover, a deflection amount of 1.6 mm to 1.8 mm is measured at both X direction ends (at 8 mm and 242 mm in the X direction), particularly at the Y direction 8 mm location, in the press portion 32.

Figure 20B:
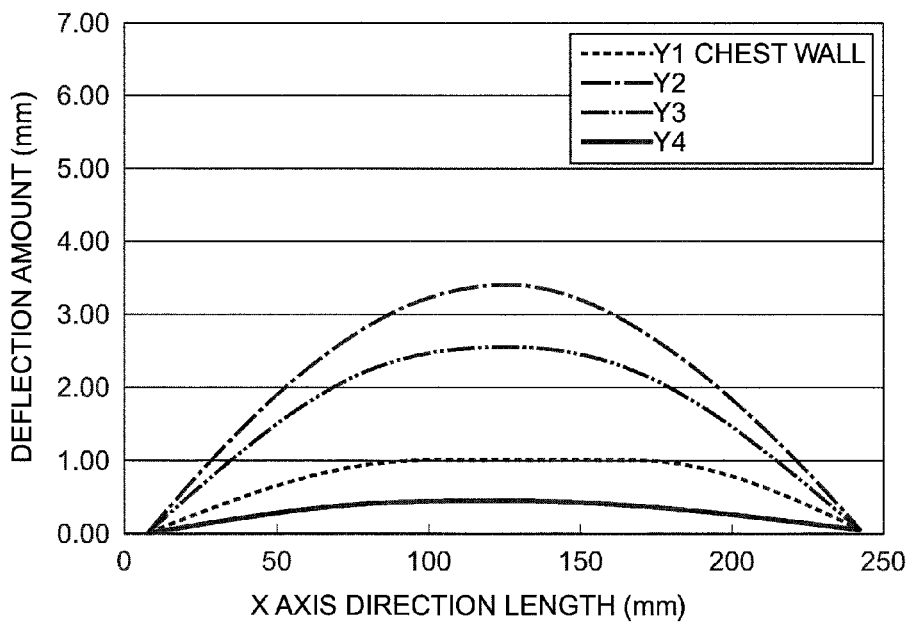
FIG. 20B is a graph illustrating a relationship between X axis direction length and deflection amount in a press portion of a press plate according to a Comparative Example 3.

However, as illustrated in FIG. 20B, in the press plate of Comparative Example 3, only a very small increase in deflection amount is measured under the same deflection amount measurement conditions as for the press plate 30 of Example 3. Similarly to the press plate of Comparative Example 1, the press plate of Comparative Example 3 has a deflection amount of zero at both X direction ends (at 8 mm and 242 mm in the X direction) of the press portion in a range of 8 mm to 120 mm along the Y direction.

Figure 21:
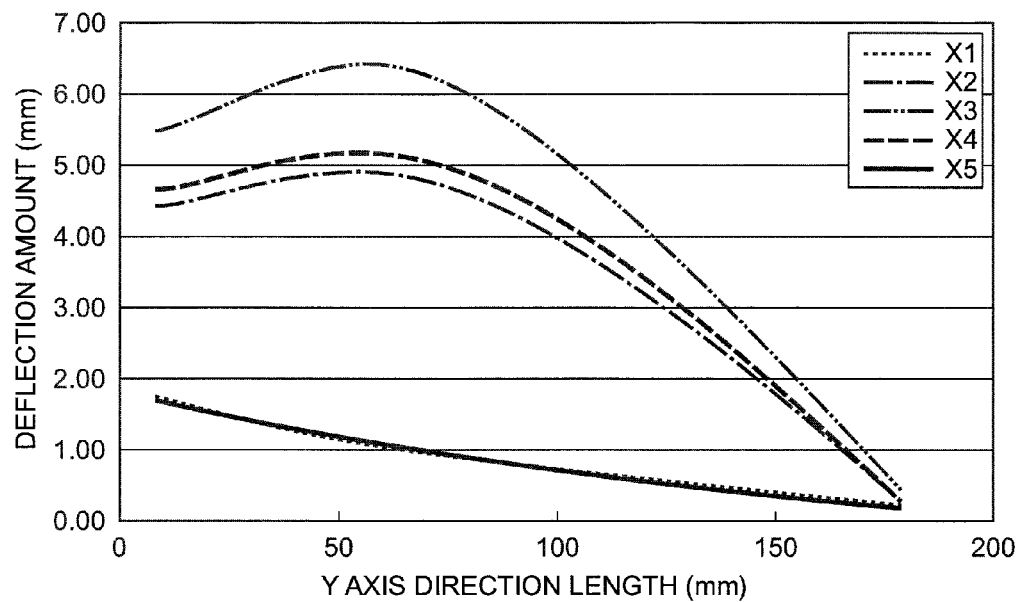
FIG. 21A is a graph illustrating a relationship between Y axis direction length (at positions from a chest wall to an opposite side thereto) and deflection amount in the press portion according to Example 3.
FIG. 21B is a graph illustrating a relationship between Y axis direction length and deflection amount in the press portion according to Comparative Example 3.
Figure 21:
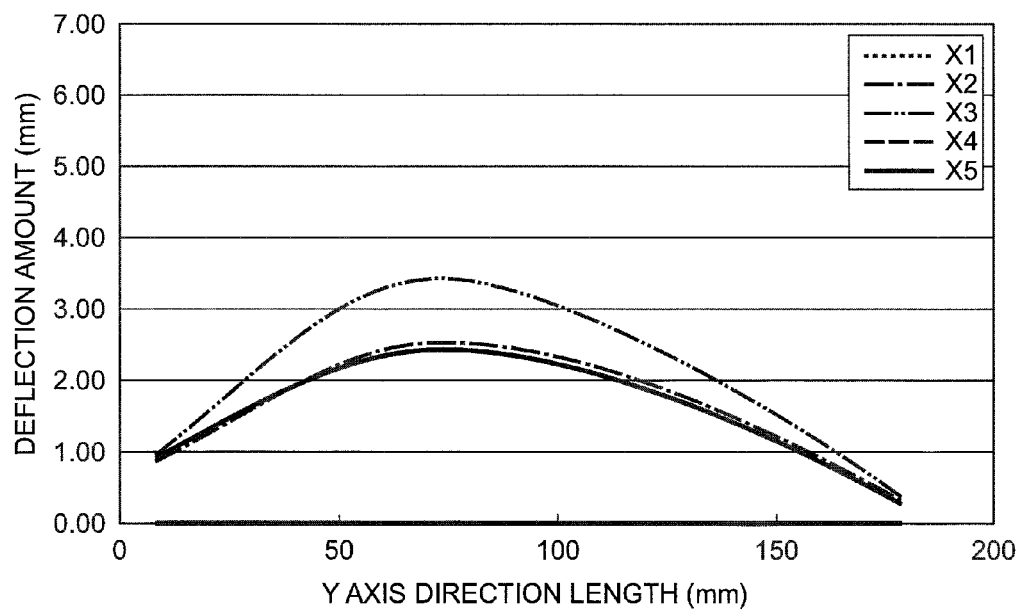

FIG. 21A illustrates a relationship between a deflection amount in mm of the press portion 32 and positions (Y direction positions) in mm from a coordinate origin at an edge portion of the press portion 32 where the second wall portion 36B stands up in the press plate 30 of Example 3. Data X1 shows the deflection amount at a position 8 mm in the X direction from the coordinate origin side, data X2 shows the deflection amount at an X direction 67 mm position, data X3 shows the deflection amount at an X direction 125 mm position, data X4 shows the deflection amount at an X direction 183 mm position, and data X5 shows the deflection amount at an X direction 242 mm position. The weight used to measure the deflection amount has a weight of 123N.

As illustrated in FIG. 21A, in the press plate 30 the maximum deflection amount of the press portion 32 is measured at an X direction intermediate portion, and a deflection amount is measured at all X direction positions (data X1 to data X5) at a chest wall side (8 mm in the Y direction) position. In particular, deflection on the chest wall side (8 mm in the Y direction) position is confirmed at both X direction end positions (at 8 mm and 242 mm in the X direction).

Figure 24A:
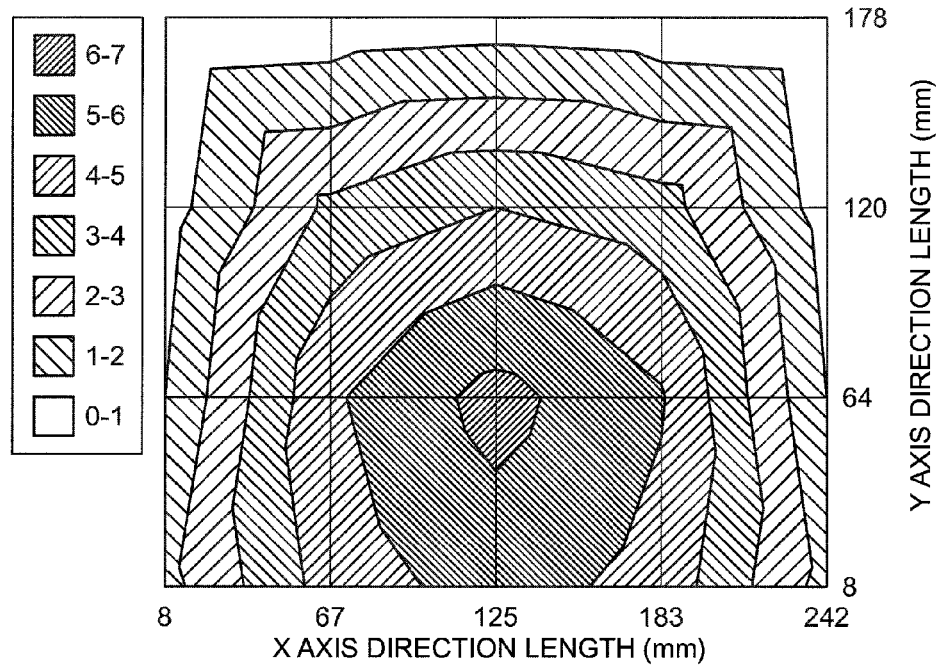
FIG. 24A is a deflection amount distribution diagram of the press portion according to Example 3.

FIG. 24A is a distribution diagram of deflection amounts of the press portion 32 of the press plate 30 of Example 3. As illustrated in FIG. 24A, deflection is confirmed up to the Y direction 8 mm (data Y1) position, namely deflection is confirmed up to the chest wall side, and deflection is also confirmed at the second wall portions 36A, 36B at both X direction end portions (at 8 mm and 242 mm in the X direction).

Figure 24B:
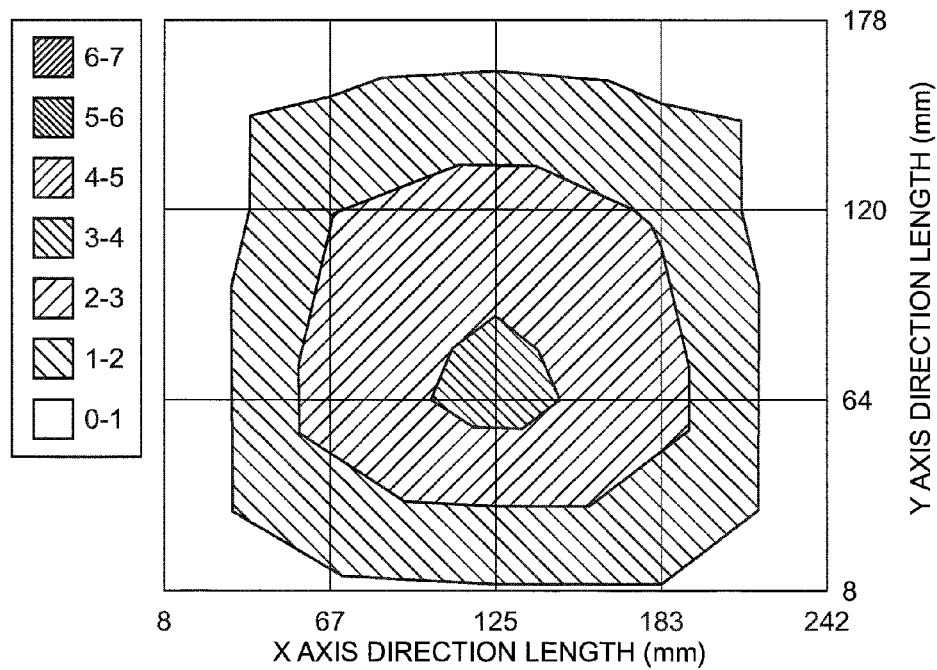
FIG. 24B is a deflection amount distribution diagram of the press portion according to Comparative Example 3.

However, as illustrated in FIG. 21B, in the press plate of Comparative Example 3, under the same deflection amount measurement conditions as those for the press plate 30 of Example 3, a very small deflection amount is measured at chest wall side (at 8 mm in the Y direction) positions at X direction intermediate portions (data X2 to data X4). However, deflection is not confirmed at chest wall side (at 8 mm in the Y direction) positions at both X direction end positions (at 8 mm and 242 mm in the X direction). Very little deflection can be confirmed at the chest wall side, as illustrated in the deflection amount distribution diagram of the press portion of the press plate according to Comparative Example 3 illustrated in FIG. 24B.

Example 4 and Comparative Example 4

Figure 25A:
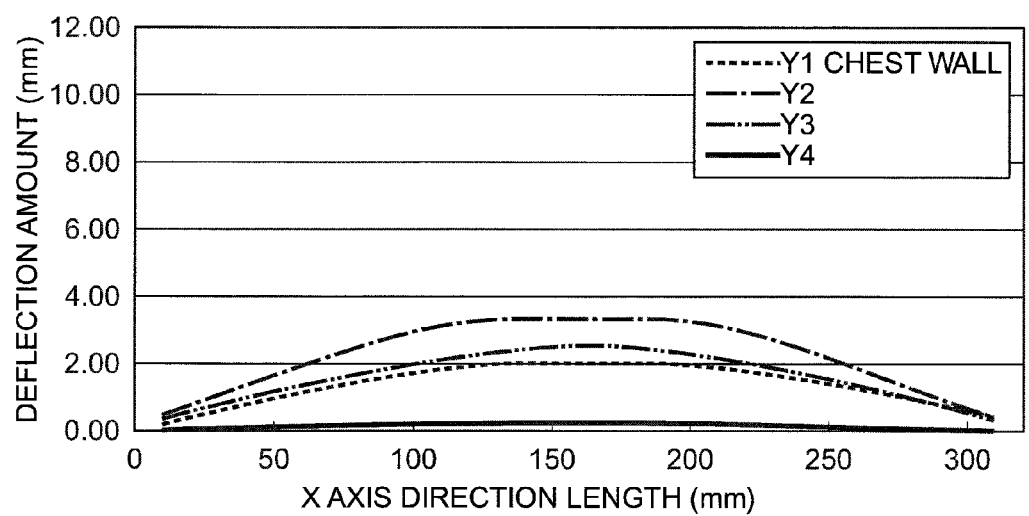
FIG. 25A is a graph illustrating a relationship between X axis direction length and deflection amount in a press portion of a press plate according to an Example 4 of the first exemplary embodiment.

FIG. 25A illustrates a relationship between a deflection amount in mm of the press portion 32 and positions (X direction positions) in mm from a coordinate origin at an edge portion of the press portion 32 where the first wall portion 34A stands up in a press plate 30 of Example 4. The press portion 32 has an X direction length of 300 mm, and a Y direction length of 240 mm. Data Y1 shows the deflection amount at a Y direction 10 mm position on the chest wall side, data Y2 shows the deflection amount at a Y direction 85 mm position, data Y3 shows the deflection amount at a Y direction 160 mm position, and data Y4 shows the deflection amount at a Y direction 235 mm position. The weight used to measure the deflection amount has a weight of 33N.

As illustrated in FIG. 25A, in the press plate 30 the maximum deflection amount of the press portion 32 in excess of 3.0 mm is measured at an X direction intermediate portion at around 85 mm in the Y direction. At the X direction intermediate portion of the press portion 32, a deflection amount of slightly over half the maximum deflection amount is measured at the Y direction 10 mm (data Y1) position. For both X position ends of the press portion 32 (at 10 mm and 310 mm in the X direction), a deflection amount in excess of zero is measured in a Y direction range of 10 mm to 160 mm.

Figure 29A:
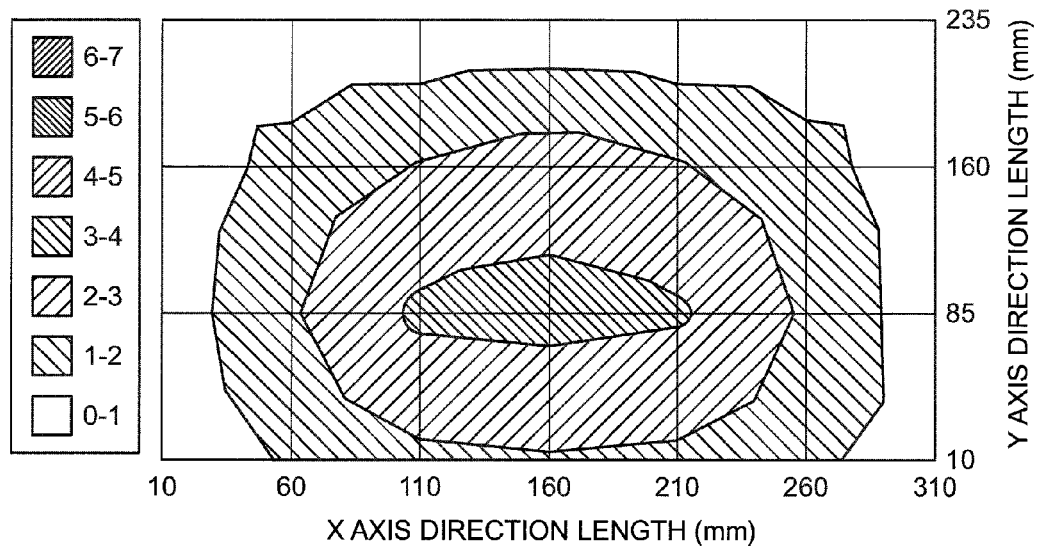
FIG. 29A is a deflection amount distribution diagram of the press portion according to Example 4.

FIG. 29A is a deflection amount distribution diagram of the press portion 32 of the press plate 30 of Example 4. As illustrated in FIG. 29A, deflection can be confirmed up to the Y direction 10 mm (data Y1) position, namely the occurrence of deflection can be confirmed up to the chest wall side.

Figure 25B:
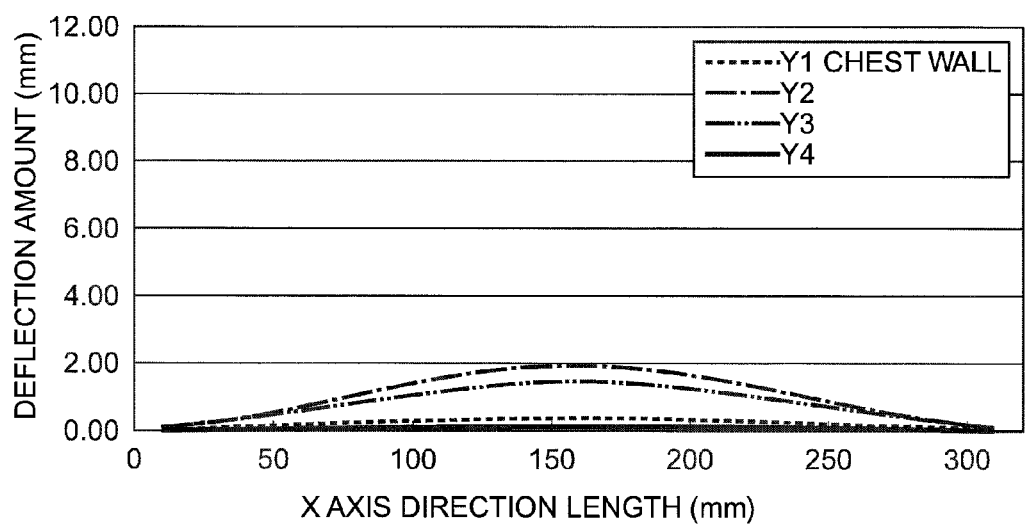
FIG. 25B is a graph illustrating a relationship between X axis direction length and deflection amount in a press portion of a press plate according to a Comparative Example 4.
Figure 29B:
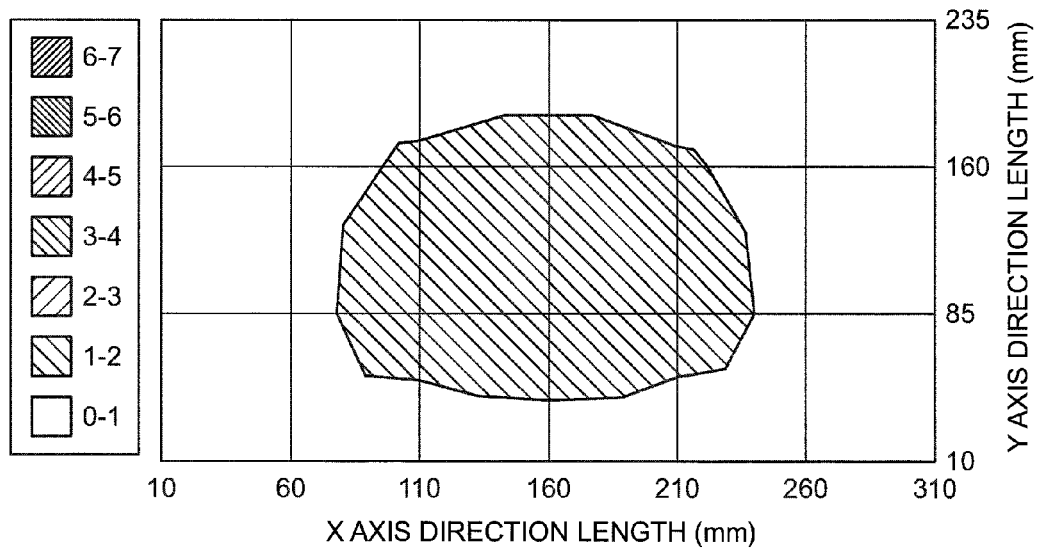
FIG. 29B is a deflection amount distribution diagram of the press portion according to Comparative Example 4.

FIG. 25B illustrates deflection amounts of a press plate of Comparative Example 4. The press plate of Comparative Example 4 is not provided with the first slit 40, the second slits 42A, 42B, the first corner portion slits 44A, 44B, or the second corner portion slits 46A, 46B of the press plate 30 of Example 4. Measurement conditions are the same. In the press plate of Comparative Example 4, the overall deflection amount is smaller than that of the press plate 30 of Example 4. Moreover, a very small deflection amount is measured for an X direction intermediate portion of the press portion at a Y direction position of 10 mm (data Y1). However, at both X direction ends of the press portion (at 10 mm and 310 mm in the X direction), the deflection amount is zero in a Y direction range of 10 mm to 160 mm. Deflection cannot be confirmed at the chest wall side, as illustrated in the deflection amount distribution diagram of the press portion of the press plate according to Comparative Example 4 illustrated FIG. 29B.

Example 5 and Comparative Example 5

Figure 26A:
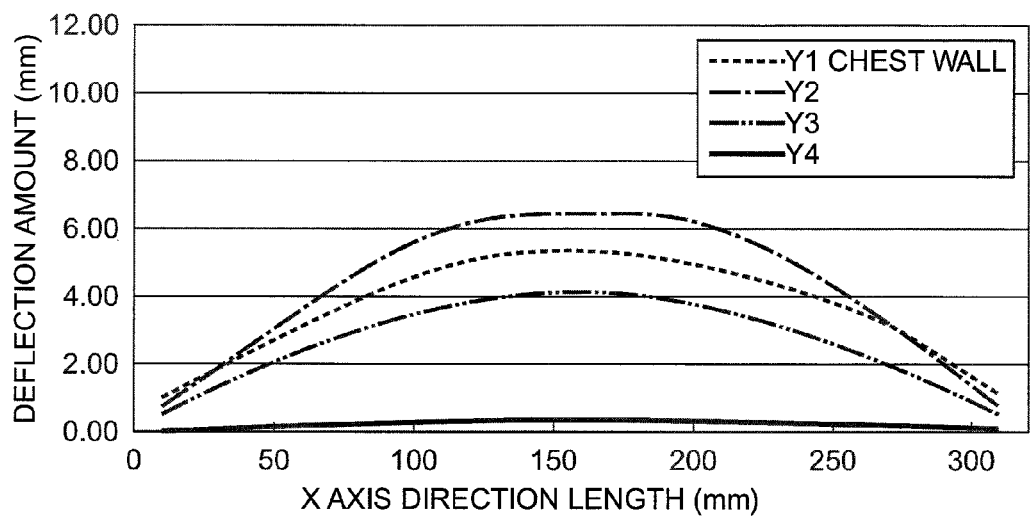
FIG. 26A is a graph illustrating a relationship between X axis direction length and deflection amount in a press portion of a press plate according to an Example 5 of the first exemplary embodiment.

FIG. 26A illustrates a relationship between a deflection amount in mm of the press portion 32 and positions in mm along an edge portion of the press portion 32 in a press plate 30 of Example 5. Note that the size and Y direction measurement positions of the press portion 32 are the same as in Example 4. The weight used in measuring the deflection amount has a weight of 78N. As illustrated in FIG. 26A, overall an increased deflection amount is measured in the press plate 30 according to the weight. The increasing deflection trend is similar to that of the press plate 30 of Example 4, however at an X direction intermediate portion of the press portion 32, a deflection amount of 82% to 84% of the maximum deflection amount is measured for the Y direction 10 mm (data Y1) position. Moreover, a deflection amount of nearly 1.0 mm is measured at both X direction ends (at 10 mm and 310 mm in the X direction), particularly at the Y direction 10 mm location, in the press portion 32.

Figure 30A:
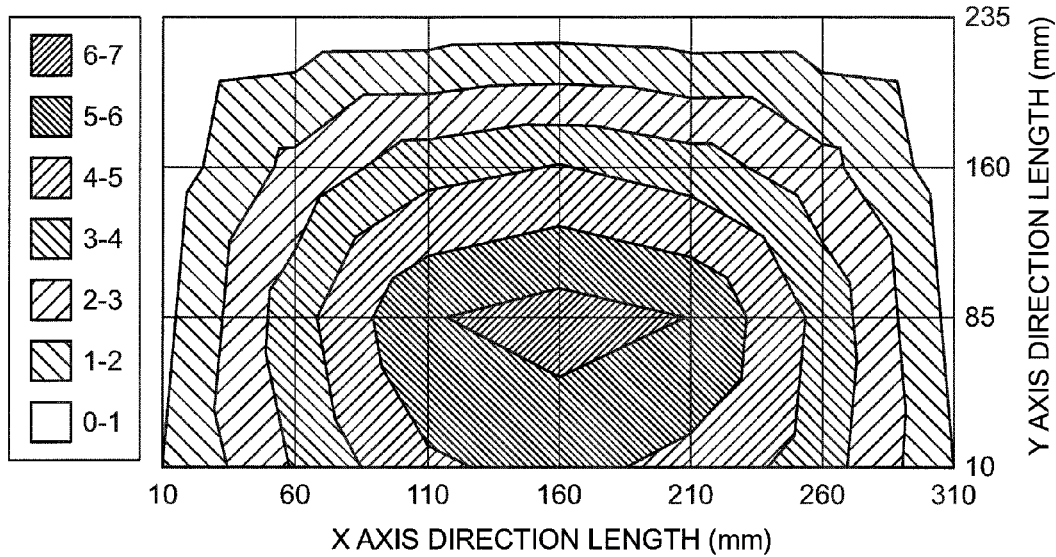
FIG. 30A is a deflection amount distribution diagram of the press portion according to Example 5.

FIG. 30A is a deflection amount distribution diagram for the press portion 32 of the press plate 30 according to Example 5. As illustrated in FIG. 30A, deflection can be confirmed up to the Y direction 10 mm (data Y1) position, namely deflection can be confirmed up to the chest wall side. It can also be confirmed that deflection occurs at both X direction ends (at 10 mm and 310 mm in the X direction).

Figure 26B:
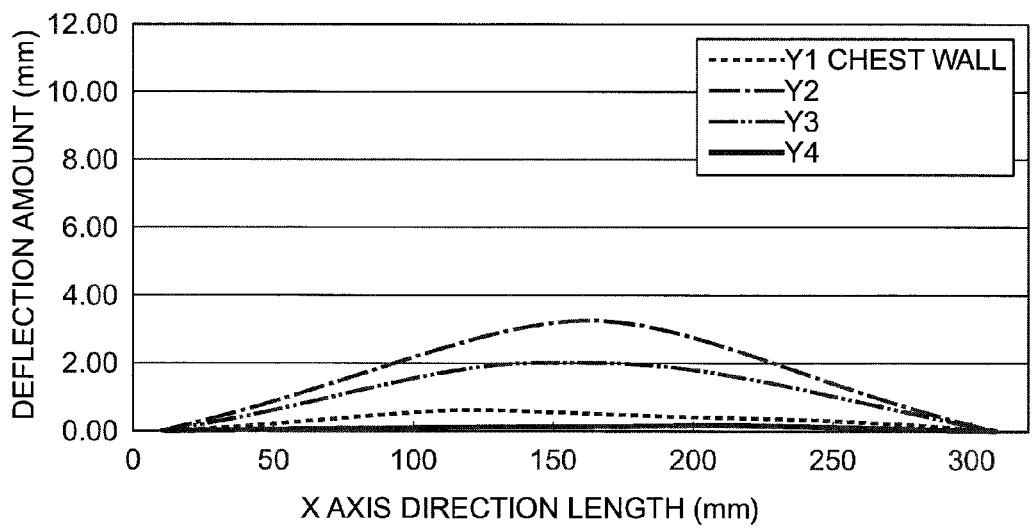
FIG. 26B is a graph illustrating a relationship between X axis direction length and deflection amount in a press portion of a press plate according to a Comparative Example 5.
Figure 30B:
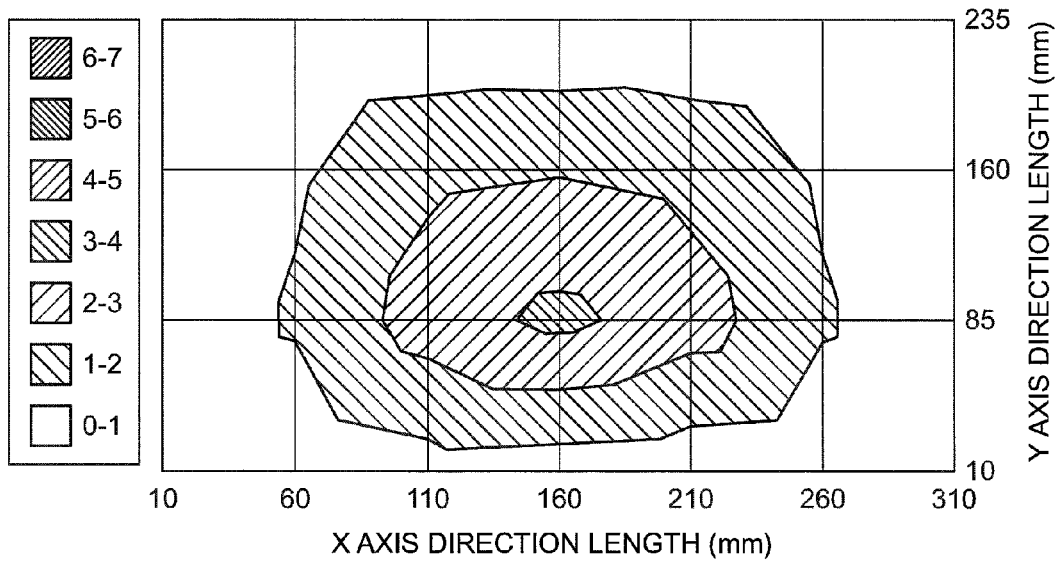
FIG. 30B is a deflection amount distribution diagram of the press portion according to Comparative Example 5.

However, as illustrated in FIG. 26B, in the press plate of Comparative Example 5, only a very small increase in deflection amount is measured under the same deflection amount measurement conditions as for the press plate 30 of Example 5. Similarly to the press plate of Comparative Example 4, the press plate of Comparative Example 5 has a deflection amount of zero at both X direction ends (at 10 mm and 310 mm in the X direction) of the press portion in a range of 10 mm to 160 mm along the Y direction. Deflection at the chest wall side cannot be confirmed, as illustrated in the deflection amount distribution diagram of the press portion of the press plate according to Comparative Example 5 illustrated FIG. 30B.

Example 6 and Comparative Example 6

Figure 27A:
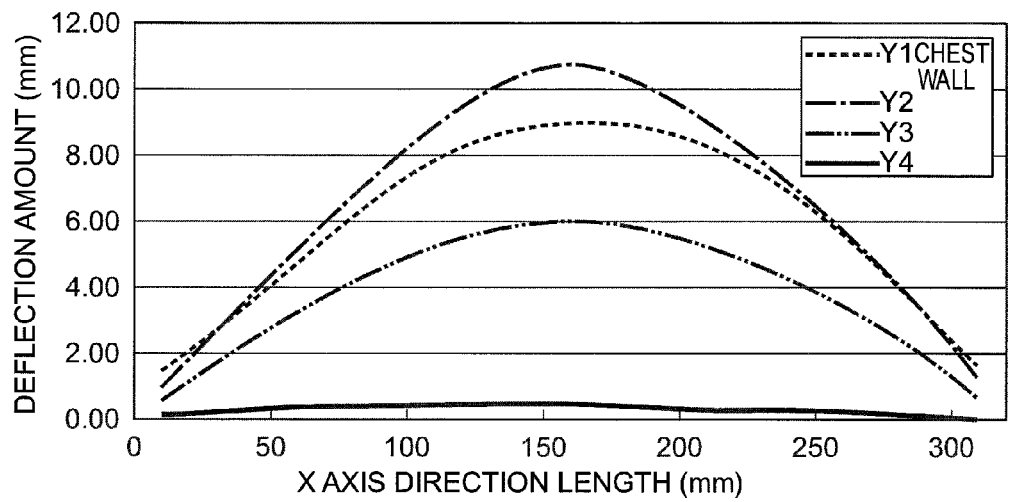
FIG. 27A is a graph illustrating a relationship between X axis direction length and deflection amount in a press portion of a press plate according to an Example 6 of the first exemplary embodiment.

FIG. 27A illustrates a relationship between a deflection amount in mm of the press portion 32 and positions in mm along an edge portion of the press portion 32 in a press plate 30 of Example 6. Note that the size and Y direction measurement positions of the press portion 32 are the same as in Example 4. The weight used in measuring the deflection amount has a weight of 123N. As illustrated in FIG. 27A, overall an increased deflection amount is measured in the press plate 30 according to the applied weight. The increasing deflection trend is similar to that of the press plates 30 of Example 4 and Example 5, however at an X direction intermediate portion of the press portion 32, a deflection amount of 82% to 84% of the maximum deflection amount is measured for the Y direction 10 mm (data Y1) position. Moreover, a deflection amount of 1.4 mm to 1.7 mm is measured at both X direction ends (at 10 mm and 310 mm in the X direction), particularly at the Y direction 10 mm location, in the press portion 32.

Figure 27B:
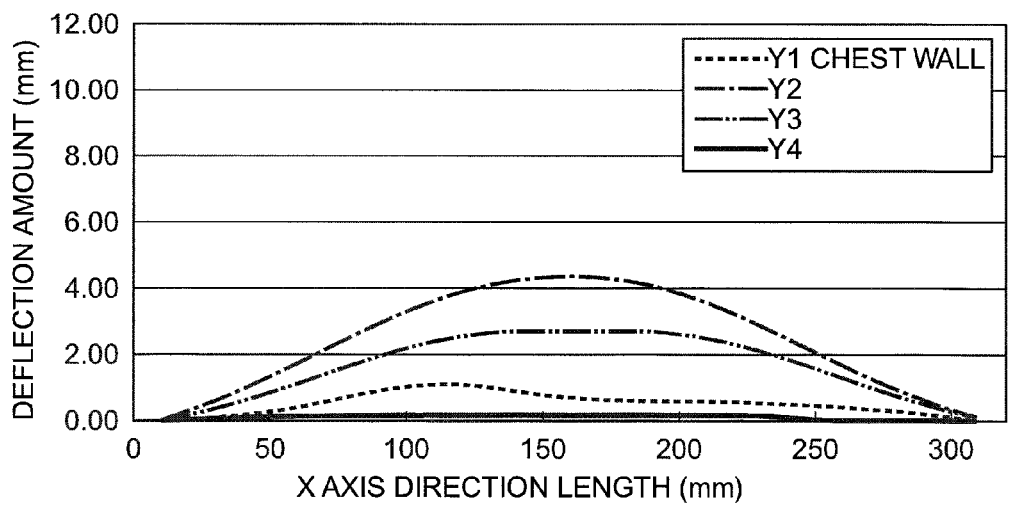
FIG. 27B is a graph illustrating a relationship between X axis direction length and deflection amount in a press portion of a press plate according to a Comparative Example 6.

However, as illustrated in FIG. 27B, in the press plate of Comparative Example 6 only a very small increase in deflection amount is measured under the same deflection amount measurement conditions as for the press plate 30 of Example 6. Similarly to the press plate of Comparative Example 4, the press plate of Comparative Example 6 has a deflection amount of zero at both X direction ends (at 10 mm and 310 mm in the X direction) of the press portion in a range of 10 mm to 160 mm along the Y direction.

Figure 28A:
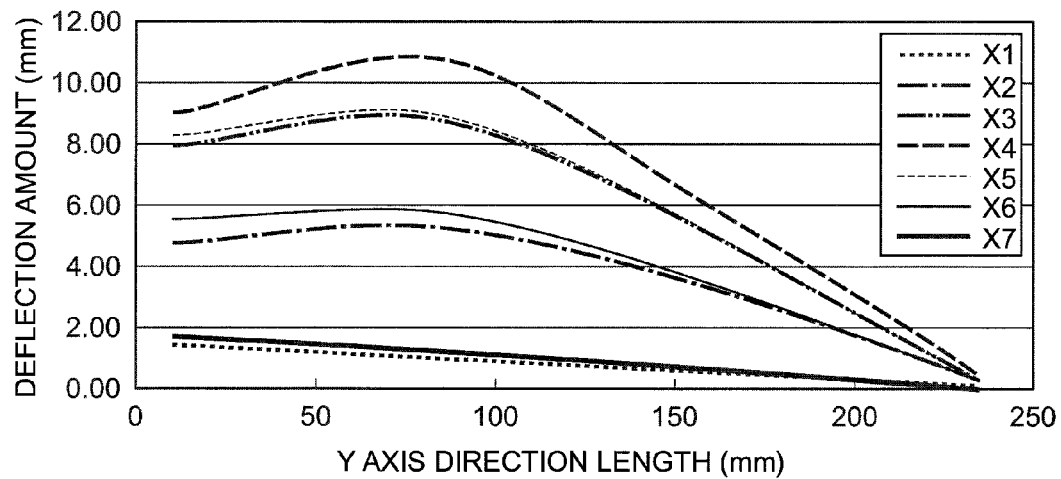
FIG. 28A is a graph illustrating a relationship between Y axis direction length and deflection amount in the press portion according to Example 6.
Figure 28B:
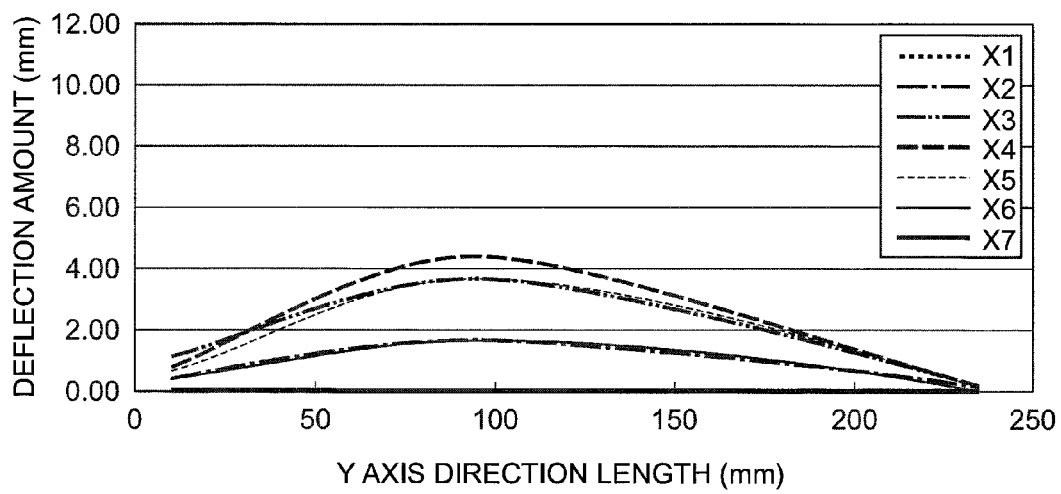
FIG. 28B is a graph illustrating a relationship between Y axis direction length and deflection amount in the press portion according to Comparative Example 6.

FIG. 28A illustrates a relationship between a deflection amount in mm of the press portion 32 and positions (Y direction positions) in mm from a coordinate origin at an edge portion of the press portion 32 where the second wall portion 36A stands up in the press plate 30 of Example 6. Data X1 shows the deflection amount at a position 10 mm in the X direction from the coordinate origin side, data X2 shows the deflection amount at an X direction 60 mm position, data X3 shows the deflection amount at an X direction 110 mm position, data X4 shows the deflection amount at an X direction 160 mm position, data X5 shows the deflection amount at an X direction 210 mm position, data X6 shows the deflection amount at an X direction 260 mm position, and data X7 shows the deflection amount at an X direction 310 mm position. The weight used to measure the deflection amount has a weight of 123N.

As illustrated in FIG. 28A, in the press plate 30 the maximum deflection amount of the press portion 32 is measured at an X direction intermediate portion (data X4) of the press portion 32, and a deflection amount is measured at all X direction positions (data X1 to data X7) at a chest wall side (10 mm in the Y direction) position. In particular, deflection is confirmed at both X direction end positions (at 10 mm and 310 mm in the X direction) at the chest wall side (10 mm in the Y direction) position.

Figure 31A:
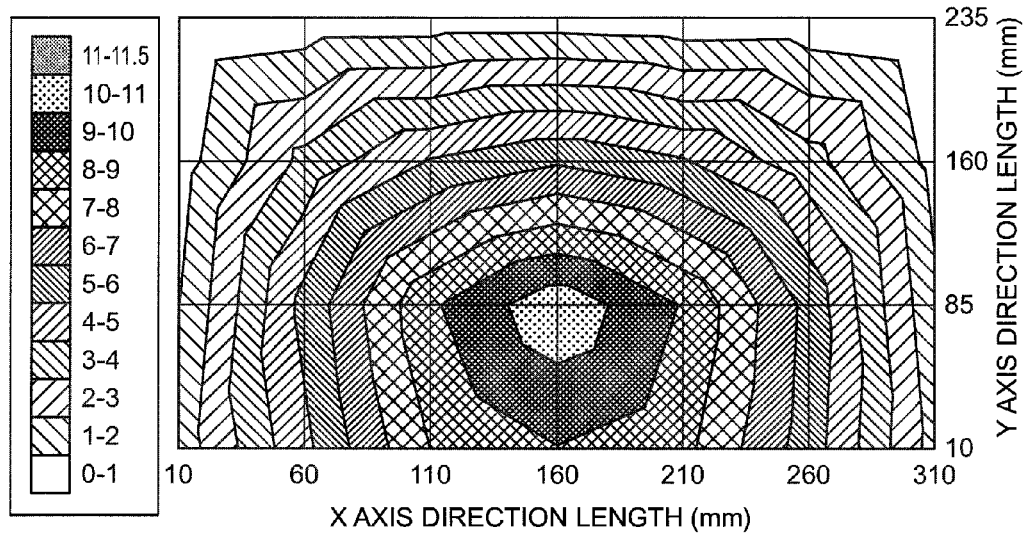
FIG. 31A is a deflection amount distribution diagram of the press portion according to Example 6.

FIG. 31A is a distribution diagram of deflection amount of the press portion 32 of the press plate 30 of Example 6. As illustrated in FIG. 31A, deflection can be confirmed up to the Y direction 10 mm (data Y1) position, namely deflection can be confirmed up to the chest wall side, and the occurrence of deflection can also be confirmed at the second wall portions 36A, 36B at both X direction end portions (at 10 mm and 310 mm in the X direction).

Figure 31B:
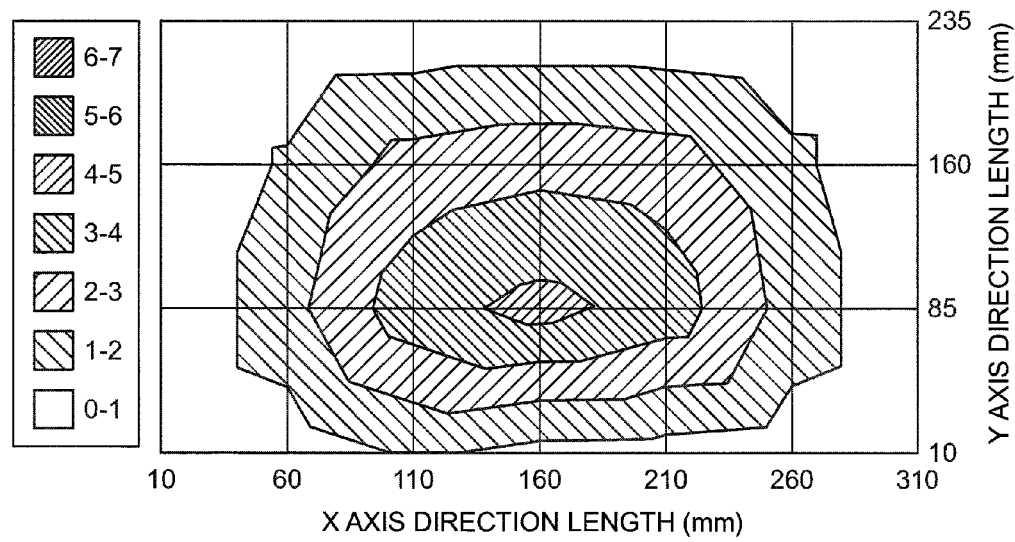
FIG. 31B is a deflection amount distribution diagram of the press portion according to Comparative Example 6.

However, as illustrated in FIG. 27B, under the same deflection amount measurement conditions as those for the press plate 30 of Example 6, in the press plate of Comparative Example 6, a very small deflection amount is measured at the chest wall side (at 10 mm in the Y direction) position at X direction intermediate portions (data X2 to data X6). However, deflection is not confirmed at chest wall side (at 10 mm in the Y direction) position at both X direction end positions (at 10 mm and 310 mm in the X direction). Very little deflection can be confirmed at the chest wall side, as illustrated in the deflection amount distribution diagram of the press portion of the press plate according to Comparative Example 6 illustrated in FIG. 31B.

Operation and Advantageous Effects of the First Exemplary Embodiment

In the press plate 30 of the first exemplary embodiment, the first wall portion 34A stands up at one edge portion, and the second wall portions 36A, 36B stand up at other edge portions of the plate shaped press portion 32. The first slit 40 is provided extending along the first wall portion 34A, and the second slits 42A, 42B are provided extending along the second wall portions 36A, 36B. When the compression force F1 compressing for example the breast N of the examinee W is applied to the press portion 32 from the support body 33, the reaction force F2 is applied to the press portion 32 from the breast N. The rigidity of the first wall portion 34A with respect to the reaction force F2 is reduced by the first slit 40, and locations on the first wall portion 34A between the first slit 40 and the press portion 32 are capable of deformation, such that deflection of the press portion 32 occurs. Similarly, the rigidity of the second wall portions 36A, 36B is reduced by the second slits 42A, 42B, enabling deformation of locations on the second wall portions 36A, 36B between the second slits 42A, 42B and the press portion 32, such that deflection of the press portion 32 occurs.

The compression force F1 applied to the support body 33 from the press portion 32 is concentrated at the corner portions 38A, 38B between the first wall portion 34A and the second wall portions 36A, 36B. Moreover, the rigidity of the corner portions 38A, 38B would normally be higher than the rigidity of the first wall portion 34A and the second wall portions 36A, 36B respectively. The first corner portion slits 44A, 44B are provided straddling the corner portions 38A, 38B of the support body 33, with the first corner portion slits 44A, 44B reducing the rigidity of the corner portions 38A, 38B. Locations of the support body 33 between the first corner portion slits 44A, 44B and the press portion 32 are accordingly also capable of deformation at the corner portions 38A, 38B, such that deflection of the press portion 32 occurs. Accordingly, since the overall rigidity of the support body 33 can be made substantially uniform, the compression force F1 from the press portion 32 can be made substantially uniform. Appropriate deflection of the press portion 32 occurs at the first wall portion 34A, the second wall portions 36A, 36B, and the corner portions 38A, 38B. For example, appropriate deflection of the press portion 32 occurs so as to surround the breast N when compressing the breast N with the press plate 30.

The first corner portion slits 44A, 44B are moreover connected to the first slit 40 and are at separations to the second slits 42A, 42B. The rigidity of the first wall portion 34A is reduced at the connection locations of the first corner portion slits 44A, 44B with the first slit 40, such that appropriate deflection of the press portion 32 occurs. The separation locations between the first corner portion slits 44A, 44B and the second slits 42A, 42B configure support portions that couple together and support the upper and lower locations of the support body 33 that are separated by the second slits 42A, 42B. Accordingly, when the compression force F1 is being applied to the support body 33, the upper and lower locations of the support body 33 are supported at the separation locations, enabling distortion of the support body 33 between the upper and lower locations to be effectively suppressed. Moreover, the compression force F1 that is concentrated at the corner portions 38A, 38B of the support body 33 circumvents the first corner portion slits 44A, 44B and is applied to the press portion 32 through the separation locations. The compression force F1 is accordingly dispersed in the transmission process and applied to the press portion 32 such that the compression force F1 can be made more uniform in the press portion 32.

The press plate 30 of the first exemplary embodiment is provided with the second corner portion slits 46A, 46B disposed at separations to and parallel to the first corner portion slits 44A, 44B. The plural first corner portion slits 44A, 44B and second corner portion slits 46A, 46B are provided to the corner portions 38A, 38B. Appropriate deflection of the press portion 32 accordingly occurs since the rigidity of the corner portions 38A, 38B is further reduced.

At the corner portions 38A, 38B, the upper and lower locations of the support body 33 that are separated by the first corner portion slits 44A, 44B circumvent the first corner portion slits 44A, 44B and are coupled together by the separation locations between the first corner portion slits 44A, 44B and the second slits 42A, 42B in the second wall portions 36A, 36B. Similarly at the corner portions 38A and 38B the upper and lower locations of the support body 33 separated by the second corner portion slits 46A, 46B circumvent the second corner portion slits 46A, 46B and are coupled together by the separation locations between the second corner portion slits 46A, 46B and the first slit 40 in the first wall portion 34A. The side view profiles of the support locations at the corner portions 38A, 38B from the upper end of the support body 33 to the lower end at the press portion 32 are accordingly configured with S-shaped or crank-shaped meandering profiles. Appropriate deflection of the press portion 32 occurs since spring characteristics can be obtained at the corner portions 38A, 38B of the support body 33 within a resilient deformation range of the support body 33 along the direction in which the compression force F1 is applied and along the direction in which the reaction force F2 that occurs due to the compression force F1 is applied.

In the press plate 30 of the first exemplary embodiment, the width of the first slit 40 is set to be greater than the width of the second slits 42A, 42B, thereby reducing the rigidity of the first wall portion 34A to a greater extent than the rigidity of the second wall portions 36A, 36B. The deflection amount can accordingly be increased at the edge portion of the press portion 32 where the first wall portion 34A stands up.

According to the press plate 30 of the first exemplary embodiment, the first slit 40 is disposed above the second slits 42A, 42B, thereby enabling a region for supporting the press plate 30 to be secured at a location above the second slits 42A, 42B in the second wall portions 36A, 36B. For example, one end of the support arm 34 that supports the press plate 30 is configured so as to be attachable to this region.

According to the press plate 30 of the present exemplary embodiment, the gap members 60, 62 are provided inside the first slit 40, the second slits 42A, 42B, the first corner portion slits 44A, 44B, and the second corner portion slits 46A, 46B. The gap members 60, 62 are formed from a softer material than the material of the support body 33. The gap members 60, 62 are configured so as to be capable of elongating and compressing following shape deformation such that the gap members 60, 62 can fill the inside of the slits including the first slit 40 at all times, even when shape deformation (for example a reduction in width) of the slits including the first slit 40 occurs due to the compression force F1 and the opposing reaction force F2. The breast N of the examinee W, for example, can thereby be prevented from becoming caught inside the slits including the first slit 40.

According to the press plate 30 of the first exemplary embodiment, the gap members 60, 62 are set with a higher rigidity where they are provided to the first corner portion slits 44A, 44B and the second corner portion slits 46A, 46B than where the gap members 60, 62 are provided to the first slit 40 and the second slits 42A, 42B. The rigidity of the corner portions 38A, 38B can accordingly be raised slightly by the gap members 60, 62 when the compression force F1 is being applied to the support body 33, thereby enabling distortion of the support body 33 between the upper and lower locations of the first corner portion slits 44A, 44B and distortion between the upper and lower portions of the second corner portion slits 46A, 46B to be effectively suppressed.

According to the press plate 30 of the first exemplary embodiment, the reinforcement member 50 is provided above the first slit 40 at the inner wall face of the first wall portion 34A. The reinforcement member 50 is formed from a harder material than the material of the support body 33. Note that deflection of the edge portion of the press portion 32 where the first wall portion 34A stands up is not impeded since the reinforcement member 50 is provided to the first wall portion 34A above the first slit 40. The rigidity of the first wall portion 34A is accordingly increased by the reinforcement member 50, thereby enabling an appropriate compression force F1 to be applied to the first wall portion 34A.

In the press plate 30 of the first exemplary embodiment, the first wall portion 34A stands up at one edge portion of the resiliently deformable plate shaped press portion 32, and the second wall portions 36A, 36B stand up at other edge portions of the press portion 32. The first wall portion 34A is configured so as to be capable of deformation in the vertical direction, and the first wall portion 34A and the second wall portions 36A, 36B configure the support body 33 that supports the press portion 32. The deflection amount increasing component is provided, with the deflection amount increasing component configured to give a deflection amount of the press portion 32 that is greater than zero at the first wall portion 34A, the second wall portions 36A, 36B, and the corner portions 38A, 38B when the breast N is being compressed using the press portion 32, and also to increase the deflection amount along the one edge portion of the press portion 32 from both end portions across to a central portion of the first wall portion 34A. In the first exemplary embodiment the deflection amount increasing component is configured by at least the first slit 40, the second slits 42A, 42B, the first corner portion slits 44A, 44B, and the second corner portion slits 46A, 46B. When the breast N is being compressed by the press portion 32, the press portion 32 from which the first wall portion 34A stands up deforms running from a central portion towards the corner portions 38A, 38B from the top portion of the breast N at the chest wall side towards both ends of the breast N, such that appropriate deflection occurs in the press portion 32 so as to surround the breast N.

Moreover, in the press plate 30 of the first exemplary embodiment, the deflection amount increasing component is configured such that deflection also occurs along the second wall portions 36A, 36B at the other edge portions of the press portion 32. Accordingly, when the breast N is being compressed by the press plate 30, the press portion 32 can also deform running from the top portion of the breast N at the chest wall side towards the opposite side to the chest wall side. Appropriate deflection of the press portion 32 along the profile of the breast N accordingly occurs so as to surround the breast in 3 dimensions.

Moreover, in the press plate 30 of the first exemplary embodiment, the deflection amount increasing component is configured so as to increase the deflection amount of the press portion 32 from an outline of a range where the breast N contacts the press portion 32 across to the center of the outline. The breast N that is being compressed by the press portion 32 can accordingly be flattened.

The radiographic imaging apparatus 10 of the first exemplary embodiment can also obtain similar operation to the operation of the press plate 30 described above.

The press plate 30 of the first exemplary embodiment accordingly obtains the excellent advantageous effects of enabling distortion of the support body 33 to be effectively suppressed whilst increasing the uniformity of the rigidity of the support body 33 and increasing the uniformity of the compression force F1, as well as enabling appropriate deflection of the press portion 32. The radiographic imaging apparatus 10 of the first exemplary embodiment enables appropriate deflection of the press portion 32 so as to surround the breast N.

Second Exemplary Embodiment

Figure 32A:
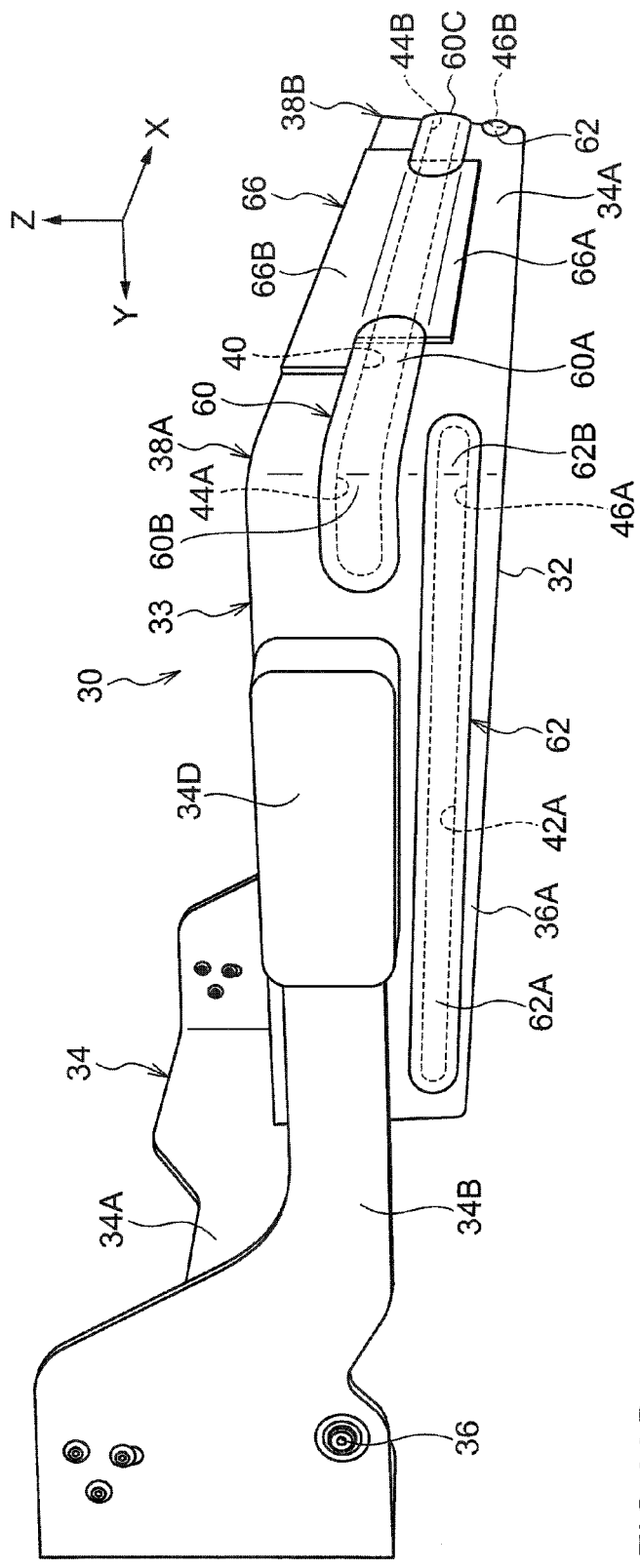
FIG. 32A is a perspective view illustrating a press plate and a support arm according to a second exemplary embodiment of the present invention.
Figure 32B:
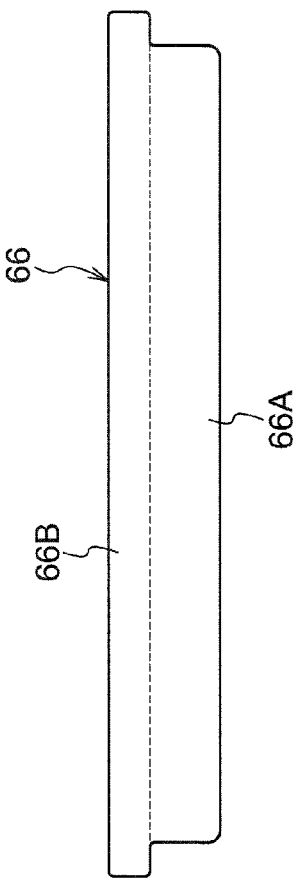
FIG. 32B is a front face view illustrating a slit cover provided to the press plate illustrated in FIG. 32A.

In the second exemplary embodiment of the present invention, an example is described in which in the press plate 30 of the first exemplary embodiment a slit cover is provided in place of the gap member 60A that is provided to the first slit 40 of the first exemplary embodiment. As illustrated in FIG. 32A and FIG. 32B, in a press plate 30 according to the second exemplary embodiment, an outer wall face of the first wall portion 34A is provided with a slit cover 66 that covers the first slit 40 and is fixed above the first slit 40. The slit cover 66 is disposed with length direction along the X direction, with a fixing location 66B configured so as to be slightly longer than a location 66A that covers the first slit 40. The slit cover 66 is formed in a T-shaped plate shape as viewed from the examinee W side. Carbon fiber reinforced plastic or carbon fiber reinforced glass, for example, is employed for the slit cover 66 from the perspectives of radiation permeability and mechanical strength. An adhesion medium such as double-sided adhesive tape, or an adhesive (for example an epoxy resin adhesive) is employed for fixing the slit cover 66. The slit cover 66 may also be fixed using a welding method that adheres at the molecular level, in which at least one out of the slit cover 66 and the first wall portion 34A is heated and melted and then cooled.

Note that the first corner portion slit 44A of the corner portion 38A is provided with a gap member 60B, and the first corner portion slit 44B of the corner portion 38B is provided with a gap member 60C. Since nothing is provided to the first slit 40, a space is configured inside the first slit 40. In the press plate 30 of the second exemplary embodiment, the rigidity of the corner portion 38A is accordingly slightly raised by the gap member 60B provided to the first corner portion slit 44A, and the rigidity of the corner portion 38C is slightly raised by the gap member 60C provided to the first corner portion slit 44B.

According to the press plate 30 of the second exemplary embodiment, the slit cover 66 is provided covering the first slit 40 at the outer wall face of the first wall portion 34A. The slit cover 66 is fixed to the first wall portion 34A above the first slit 40. The slit cover 66 accordingly prevents the breast N of the examinee W from becoming caught in the inside the first slit 40. The inside of the first slit 40 is moreover configured as a space, and the slit cover 66 is not fixed to the first wall portion 34A below the first slit 40. A location of the first wall portion 34A below the first slit 40 (a location of the first wall portion 34A from the first slit 40 to the press portion 32) is accordingly configured so as to deform readily, such that appropriate deflection of the press portion 32 occurs.

Third Exemplary Embodiment

Figure 33:
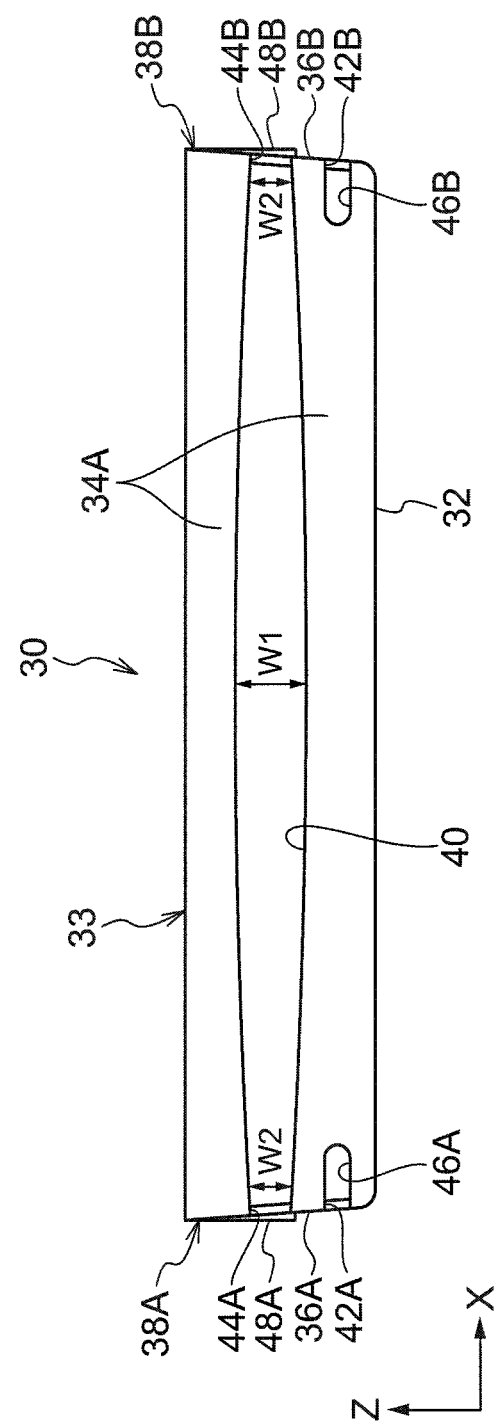
FIG. 33 is a front face view of a press plate according to a third exemplary embodiment of the present invention.

In the third exemplary embodiment of the present invention, explanation is given regarding an example in which the shape of the first slit 40 of the press plate 30 of the first exemplary embodiment has been changed. As illustrated in FIG. 33, in the press plate 30 according to the third exemplary embodiment the width of the first slit 40 is set larger at an intermediate portion than at both end portions of the first wall portion 34A. Namely, a width W1 of the intermediate portion is set larger than a width W2 of both ends of the first slit 40.

According to the thus configured press plate 30 of the third exemplary embodiment, the rigidity of the intermediate portion of the first wall portion 34A is reduced more than the rigidity of both end portions of the first wall portion. The deflection amount at a location corresponding to the intermediate portion of the first wall portion 34A can accordingly be increased at the edge portion of the press portion 32 where the first wall portion 34A stands up.

Fourth Exemplary Embodiment

Figure 34:
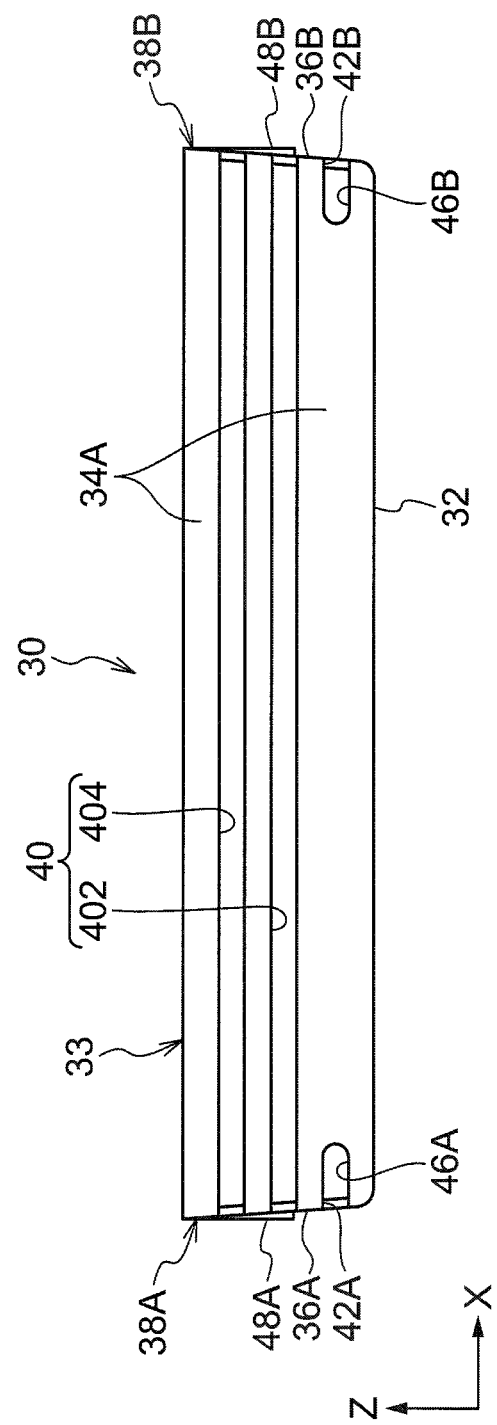
FIG. 34 is a front face view of a press plate according to a fourth exemplary embodiment of the present invention.

In the fourth exemplary embodiment of the present invention, explanation is given regarding an example in which the press plate 30 of the first exemplary embodiment is provided with a greater number of the first slits 40. As illustrated in FIG. 34, in the press plate 30 of the fourth exemplary embodiment, a greater number of the first slits 40 are provided than the number of the second slits 42A that are provided to the second wall portion 36A and second slits 42B provided to the second wall portion 36B. Plural first slits 40 are configured by a first slit 402 and a first slit 404 arrayed parallel to each other at separations in the vertical direction of the first wall portion 34A. The first slit 402 and the first slit 404 are each configured with a width of about half the width of the first slit 40 of the press plate 30 according to the first exemplary embodiment. The first slit 402, the first slit 404, the second slit 42A and the second slit 42B therefore have substantially the same width dimensions as each other. Note that configuration may also be made with 3 or more of the first slits 40.

According to the thus configured press plate 30 of the fourth exemplary embodiment, the rigidity of the first wall portion 34A is reduced to a greater extent than the rigidity of the second wall portions 36A, 36B due to disposing more of the first slits 40 than the second slits 42A and the second slits 42B. The deflection amount can accordingly be increased at the edge portion of the press portion 32 where the first wall portion 34A stands up.

Fifth Exemplary Embodiment

Figure 35:
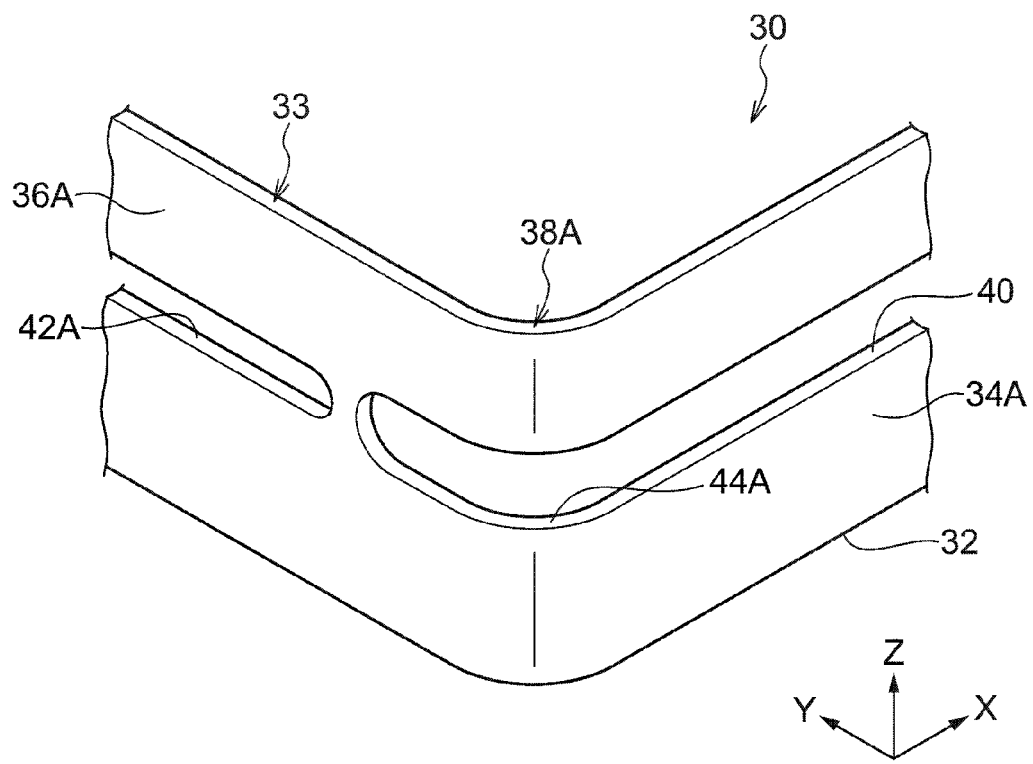
FIG. 35 is a perspective view illustrating a corner portion of a press plate according to a fifth exemplary embodiment of the present invention.

In the fifth exemplary embodiment of the present invention, explanation is given regarding a modified example of components including the second slits 42A, 42B of the press plate 30 of the first exemplary embodiment. As illustrated in FIG. 35, in the press plate 30 of the fifth exemplary embodiment, the first corner portion slit 44A provided to the corner portion 38A is connected to the first slit 40 provided in the first wall portion 34A, and is configured at a separation to the second slit 42A provided to the second wall portion 36A. The second slit 42A is disposed at a similar position to the first slit 40 with respect to the upper face of the press portion 32. In the fifth exemplary embodiment, the corner portion 38A is not provided with the second corner portion slit 46A (see for example FIG. 17). The first corner portion slit 44B provided to the corner portion 38B is similar in structure, and so explanation thereof is omitted.

The thus configured press plate 30 of the fifth exemplary embodiment obtains similar operation and advantageous effects to the operation and advantageous effects obtained by the press plate 30 of the first exemplary embodiment described above.

Sixth Exemplary Embodiment

Figure 36:
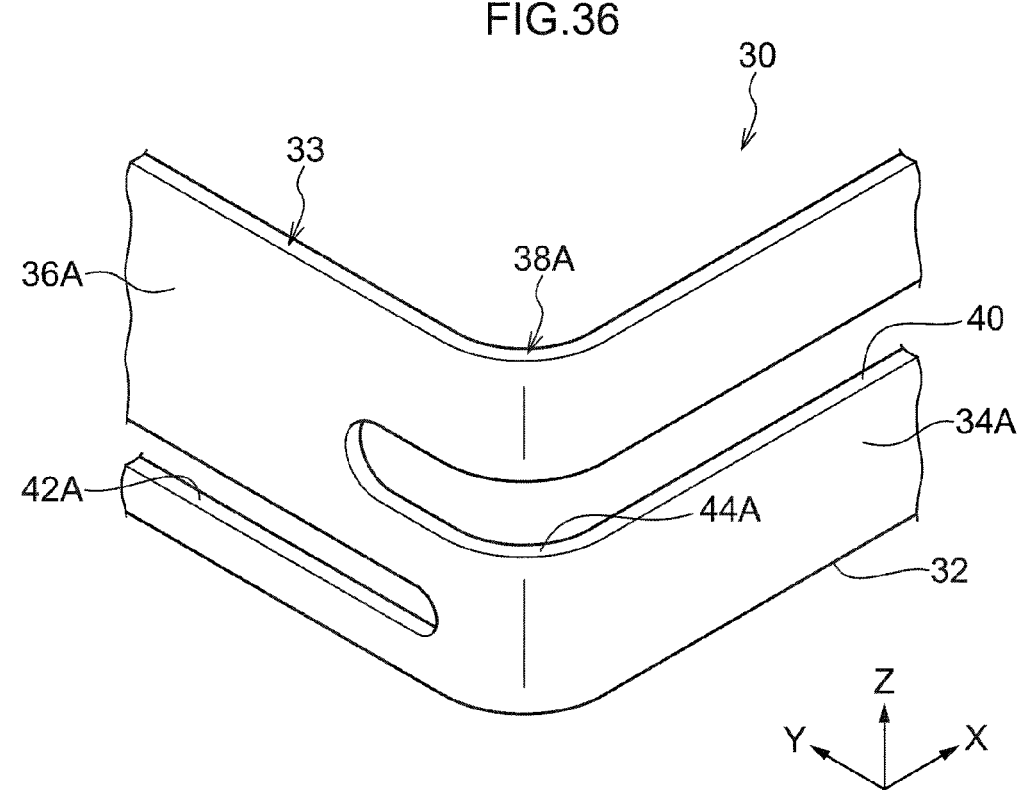
FIG. 36 is a perspective view illustrating a corner portion of a press plate according to a sixth exemplary embodiment of the present invention.

In the sixth exemplary embodiment of the present invention, explanation is given regarding a modified example of press plate 30 of the fifth exemplary embodiment. As illustrated in FIG. 36, in the press plate 30 of the sixth exemplary embodiment, the first slit 40 is disposed above the second slit 42A with respect to the upper face of the press portion 32, similarly to in the press plate 30 of the first exemplary embodiment to the fourth exemplary embodiment described above. Note that similarly to the press plate 30 of the fifth exemplary embodiment described above, the corner portion 38A is not provided with the second corner portion slit 46A. The position of the second slit 42A is displaced in the Z direction with respect to the first slit 40 and first corner portion slit 44A, thereby enabling the second slit 42A and the first corner portion slit 44A to pile up. The first corner portion slit 44B provided to the corner portion 38B is similar in structure, and so explanation thereof is omitted.

The thus configured press plate 30 of the sixth exemplary embodiment obtains similar operation and advantageous effects to the operation and advantageous effects obtained by the press plate 30 of the first exemplary embodiment described above.

Seventh Exemplary Embodiment

Figure 37:
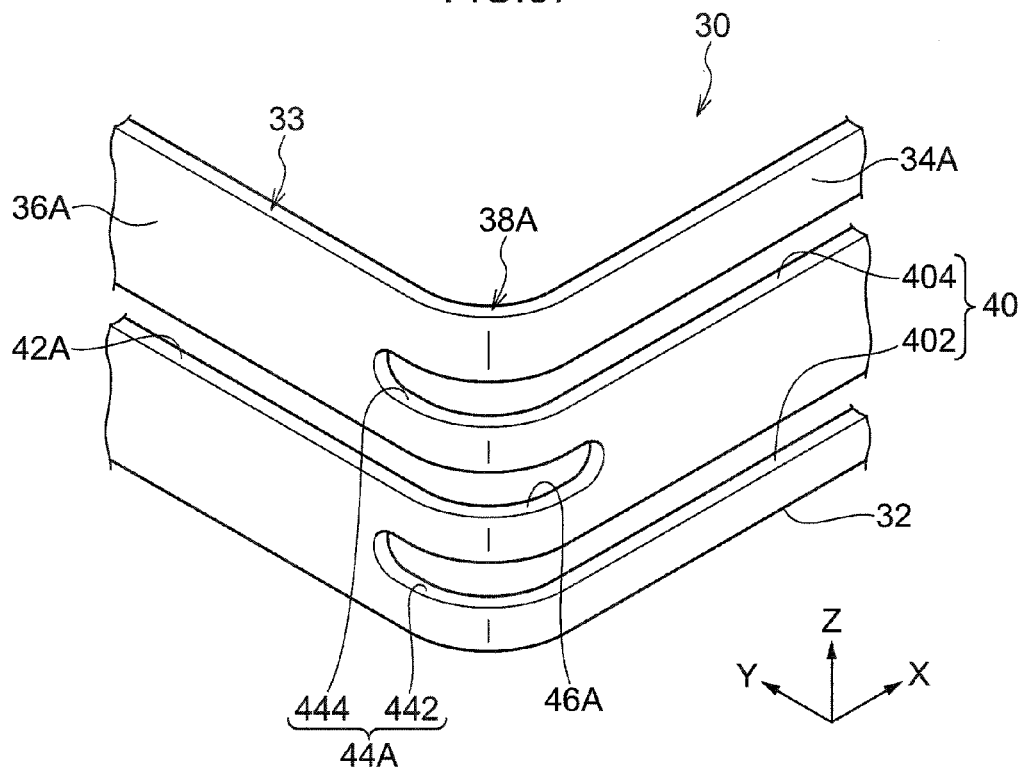
FIG. 37 is a perspective view illustrating a corner portion of a press plate according to a seventh exemplary embodiment of the present invention.

In the seventh exemplary embodiment of the present invention, explanation is given regarding a modified example of the press plate 30 of the fourth exemplary embodiment. As illustrated in FIG. 37, in the press plate 30 of the seventh exemplary embodiment first corner portion slits 44A are provided to a first slit 402 and a first slit 404 that configure plural mutually separated slits disposed parallel to each other. The second corner portion slit 46A is disposed between the first slit 402 and the first slit 404. First corner portion slits 44B provided to the corner portion 38B are similar in structure, and so explanation thereof is omitted.

In the press plate 30 of the seventh exemplary embodiment, the second corner portion slit 46A is disposed between the first slits 402, 404. The number of meanders of the meandering profile of the support location at the corner portion 38A is increased due to increasing the number of the first slits 40 that are disposed. The spring characteristics of the corner portion 38A of the support body 33 along the compression force F1 application direction and the reaction force F2 application direction can accordingly be raised further.

Eighth Exemplary Embodiment

Figure 38:
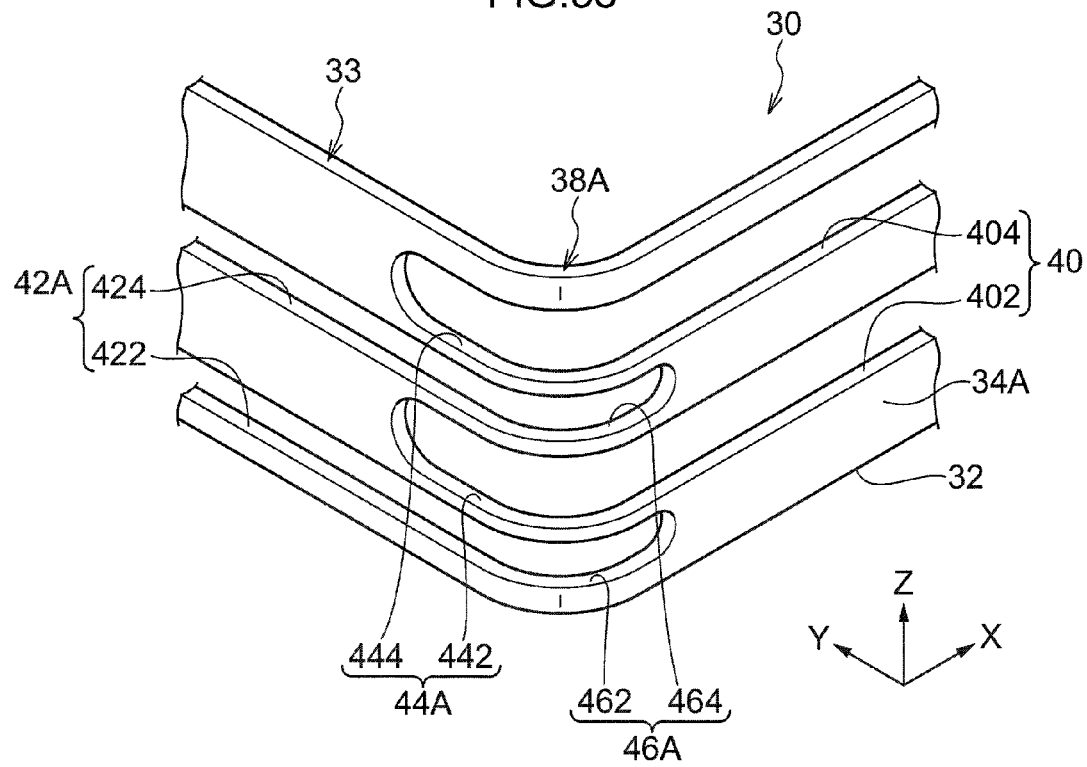
FIG. 38 is a perspective view illustrating a corner portion of a press plate according to an eighth exemplary embodiment of the present invention.

The eighth exemplary embodiment of the present invention is a modified example of the press plate 30 of the seventh exemplary embodiment. As illustrated in FIG. 38, in the press plate 30 according to the eighth exemplary embodiment the plural first slits 40 are configured by disposing the first slit 402 and the first slit 404, and plural second slits 42A are configured by disposing a second slit 422 and a second slit 424. Plural first corner portion slits 44A are configured by disposing a first corner portion slit 442 and a first corner portion slit 444, and plural second corner portion slits 46A are configured by disposing a second corner portion slit 462 and a second corner portion slit 464. The second corner portion slit 464 is disposed interposed between the first corner portion slit 442 and the first corner portion slit 444. Overall, the second corner portion slit 462, the first corner portion slit 442, the second corner portion slit 464 and the first corner portion slit 444 are alternately disposed along the Z direction. First corner portion slits 44B provided to the corner portion 38B are similar in structure, and so explanation thereof is omitted.

The thus configured press plate 30 of the eighth exemplary embodiment can obtain similar operation and advantageous effects to the operation and advantageous effects obtained by the press plate 30 according to the seventh exemplary embodiment described above.

Ninth Exemplary Embodiment

Figure 39:
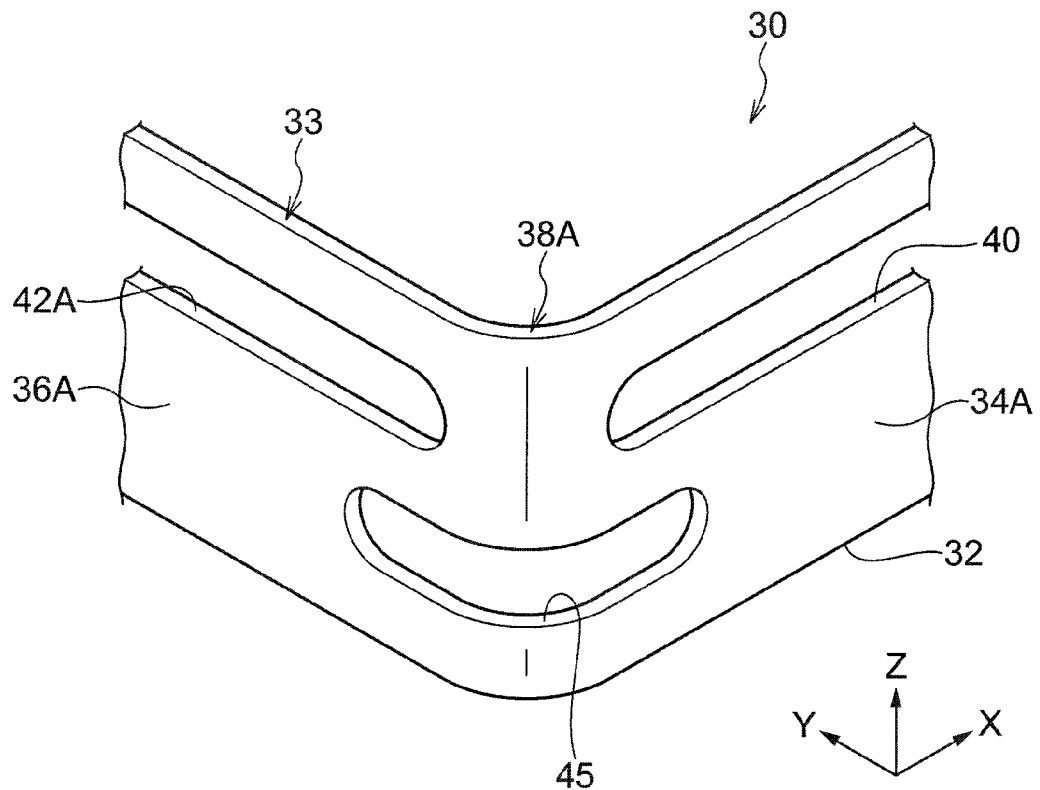
FIG. 39 is a perspective view illustrating a corner portion of a press plate according to a ninth exemplary embodiment of the present invention.

The ninth exemplary embodiment of the present invention is a modified example of the press plate 30 of the fifth exemplary embodiment. As illustrated in FIG. 39, at the corner portion 38A of a press plate 30 according to the ninth exemplary embodiment the first slit 40 and the second slit 42A are respectively disposed at a separation to each other, and a first corner portion slit 45 is disposed piling up in the Z direction. The first corner portion slit 44B provided to the corner portion 38B is similar in structure, and so explanation thereof is omitted.

The thus configured press plate 30 of the ninth exemplary embodiment is able to obtain similar operation and advantageous effects to the operation and advantageous effects obtained by the press plate 30 of the first exemplary embodiment.

Tenth Exemplary Embodiment

Figure 40:
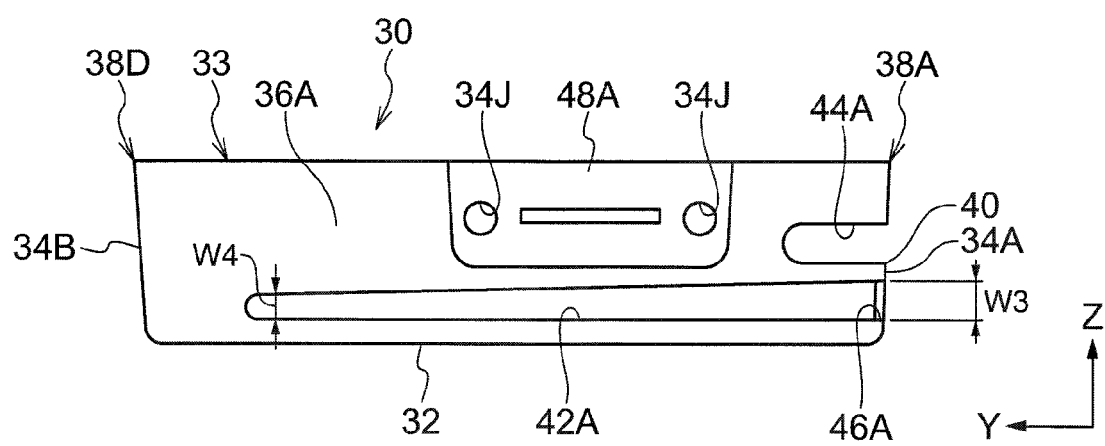
FIG. 40 is a perspective view illustrating a corner portion of a press plate according to a tenth exemplary embodiment of the present invention.

A tenth exemplary embodiment of the present invention is a modified example of the press plate 30 of the first exemplary embodiment. As illustrated in FIG. 40, in a press plate 30 according to the tenth exemplary embodiment, the second slit 42A is configured with a shape that increases in width at the first wall portion 34A side. Namely, a chest wall side width W3 of the second slit 42A is set larger than a chest wall side opposite side width W4. In the tenth exemplary embodiment, the second slit 42A is configured with a tapered shape that changes at a linear incline in side view. The second slit 42B is similar in structure, and so explanation thereof is omitted. Note that the second slit 42A may also be formed for example with a shape that changes at a curved incline, or a shape that changes at a stepped incline.

The thus configured press plate 30 according to the tenth exemplary embodiment is configured such that the width of the second slit 42A increases towards the first wall portion 34A side of the second wall portion 36A, thereby increasing the deformable range on the first wall portion 34A side of the other edge portion of the press portion 32 where the second wall portion 36A stands up. The press portion 32 is configured so as to deflect at the first wall portion 34A side about a base end at the opposite side of the second wall portion 36A to the first wall portion 34A side, thereby enabling the deflection amount of the press portion 32 to be increased on the first wall portion 34A side.

Other Exemplary Embodiments

Explanation has been given above regarding plural exemplary embodiments of the present invention, however the present invention is not limited to the above exemplary embodiments, and various changes may be made within a range not departing from the spirit of the present invention. For example, configuration may be made with a press plate 30 and a radiographic imaging apparatus 10 with a structure combing two or more of the first exemplary embodiment to the tenth exemplary embodiment described above. In particular, the gap members 60B, 60C, 62B of the press plate 30 according to the first exemplary embodiment may for example be provided to the first corner portion slits 44A, 44B and the second corner portion slits 46A, 46B of the press plate 30 of the second exemplary embodiment to the tenth exemplary embodiment. Moreover, the members such as the gap member 60B slightly raise the rigidity of the corner portions 38A, 38B, and function so as to effectively suppress distortion of the press plate 30 as explained above in paragraph [0113].

Moreover, in the press plate 30 of the first exemplary embodiment, the first slit 40 and the first corner portion slits 44A, 44B are disposed above the second slits 42A, 42B and the second corner portion slits 46A, 46B. The top-bottom relationship may be switched in the present invention. Moreover, explanation has been given regarding an example in which the radiographic imaging apparatus and the press plate of the exemplary embodiments is applied to a mammography apparatus and a press plate thereof, however there is no limitation thereto. For example, the present invention may be applied to a press plate that compresses the abdomen in order to perform X-ray imaging of an image capture body such as the stomach and intestines, and to an X-ray imaging apparatus incorporated therewith.

According to the present invention, a press plate and a radiographic imaging apparatus provided with the press plate can be obtained that are capable of increasing the uniformity of the rigidity of the support body and of increasing the uniformity of the compression force from the press portion whilst effectively suppressing distortion of the support body, as well as causing appropriate deflection of the press portion.

Moreover, according to the present invention, a press plate and a radiographic imaging apparatus provided with the press plate can be obtained that are capable of causing appropriate deflection in the press portion so as to surround a breast.

What is claimed is:

1. A press plate comprising:
a plate shaped press portion that is capable of resilient deformation;
a support body supporting the press portion, the support body comprising a first wall portion standing, from a first edge portion of the press portion, further upwards than a press portion plate face, and comprising second wall portions extending from both ends of the first wall portion to face each other along second edge portions of the press portion so as to stand up from the second edge portions;
a first slit that penetrates through the first wall portion, a length direction of the first slit extending along the first edge portion;
second slits that penetrate the second wall portions, length directions of the second slits extending along the second edge portions; and
a first corner portion slit that straddles and penetrates a corner portion between the first wall portion and the second wall portion, that is connected to the first slit, and that is not connected to the second slit.

2. The press plate of claim 1, further comprising:
a second corner portion slit that is provided straddling the corner portion, that is parallel to but not connected to the first corner portion slit, that is connected to the second slit, and that is not connected to the first slit.

3. The press plate of claim 1, wherein
the width of the first slit in the first wall portion vertical direction is larger than the width of the second slit in the second wall portion vertical direction.

4. The press plate of claim 1, wherein
a plurality of the first slits are arrayed separated from each other in the vertical direction and parallel to each other, and the number of the first slits is greater than the number of the second slits.

5. The press plate of claim 1, wherein
the first slit is disposed above the second slit with respect to the press portion plate face.

6. The press plate of claim 2, wherein
a plurality of the first corner portion slits are arrayed separated from and parallel to each other, and a second corner portion slit is disposed between each pair of the first corner portion slits.

7. The press plate of claim 3, wherein
the width of the first slit is larger at an intermediate portion of the first wall portion than at both end portions of the first wall portion.

8. The press plate of claim 2, wherein
a gap member formed from a material that is softer than the material of the support body is provided inside each of the first slit, the second slit, the first corner portion slit and the second corner portion slit.

9. The press plate of claim 8, wherein
the gap member provided at the first corner portion slit has greater rigidity than the gap member provided at the first slit, and the gap member provided at the second corner portion slit has greater rigidity than the gap member provided at the second slit.

10. The press plate of claim 1, wherein
a slit cover is provided to an outer wall face of the first wall portion, the slit cover covering the first slit and fixed above the first slit.

11. The press plate of claim 1, wherein
a reinforcement member formed from a material that is harder than the material of the support body is provided at an inner wall face of the first wall portion above the first slit.

12. The press plate of claim 3, wherein
the width of the second slit is configured to have a profile that gradually widens toward the first wall portion side.

13. A radiographic imaging apparatus comprising:
an imaging table that has an imaging face;
the press plate of claim 1 disposed with the press portion facing the imaging face;
an adjustment component that adjusts an angle of an opposing face of the imaging face with respect to the press portion;
a radiation irradiation section that is provided such that the press plate is interposed between the radiation irradiation section and the imaging table, and that irradiates radiation onto the imaging face; and
a radiation detector that is provided further towards the imaging table side than the imaging face, and that detects radiation irradiated from the radiation irradiation section that has passed through the press plate and the imaging face.

* * * * *